US011903731B2

(12) United States Patent
Kesinger et al.

(10) Patent No.: US 11,903,731 B2
(45) Date of Patent: *Feb. 20, 2024

(54) ELECTRODE ARRAY APPARATUS, NEUROLOGICAL CONDITION DETECTION APPARATUS, AND METHOD OF USING THE SAME

(71) Applicant: Forest Devices, Inc., Pittsburgh, PA (US)

(72) Inventors: Matthew Kesinger, Pittsburgh, PA (US); Dan Willis, Pittsburgh, PA (US); Stephen Norcup, Pittsburgh, PA (US); Carmelo R. Montalvo, Pittsburgh, PA (US)

(73) Assignee: Forest Devices, Inc., Pittsburgh, PA (US)

( * ) Notice: Subject to any disclaimer, the term of this patent is extended or adjusted under 35 U.S.C. 154(b) by 184 days.

This patent is subject to a terminal disclaimer.

(21) Appl. No.: 17/232,192

(22) Filed: Apr. 16, 2021

(65) Prior Publication Data
US 2021/0244355 A1 Aug. 12, 2021

Related U.S. Application Data

(63) Continuation of application No. 16/035,781, filed on Jul. 16, 2018, now Pat. No. 11,006,897.

(Continued)

(51) Int. Cl.
*A61B 5/00* (2006.01)
*A61B 5/291* (2021.01)
*A61B 5/377* (2021.01)

(52) U.S. Cl.
CPC ............ *A61B 5/6803* (2013.01); *A61B 5/291* (2021.01); *A61B 5/377* (2021.01); *A61B 5/0006* (2013.01);
(Continued)

(58) Field of Classification Search
CPC ....... A61B 5/6803; A61B 5/291; A61B 5/377; A61B 5/0006; A61B 5/6814; A61B 2560/045; A61B 2562/046
See application file for complete search history.

(56) References Cited

U.S. PATENT DOCUMENTS 4,742,831 A 5/1988 Silvian
4,846,190 A * 7/1989 John .................. A61B 5/743
600/544

(Continued)

FOREIGN PATENT DOCUMENTS

WO 2008067839 A1 6/2008
WO 2008115189 A2 9/2008
(Continued)

OTHER PUBLICATIONS

International Search Report for PCT/US2018/042363 dated Oct. 18, 2018.
(Continued)

*Primary Examiner* — Eun Hwa Kim
*Assistant Examiner* — Catherine Premraj
(74) *Attorney, Agent, or Firm* — Buchanan Ingersoll & Rooney PC

(57) ABSTRACT

An apparatus for measuring patient data includes a frame having a plurality of electrode hubs. Each hub can include one or more electrode members. The frame can be configured to receive a head of a patient. Each of the electrode hubs can have a single electrode member or a plurality of electrode members that extend from or are connected to an outer member for contacting a scalp of the head of the patient. The outer member can have at least one circuit configured to transmit data received by at least one of the electrode members to a measurement device via a wireless
(Continued)

communication connection (e.g. Bluetooth, near field communication, etc.) or a wired communication connection.

15 Claims, 20 Drawing Sheets

Related U.S. Application Data

(60) Provisional application No. 62/648,559, filed on Mar. 27, 2018, provisional application No. 62/618,273, filed on Jan. 17, 2018, provisional application No. 62/533,738, filed on Jul. 18, 2017.

(52) U.S. Cl.
CPC ....... *A61B 5/6814* (2013.01); *A61B 2560/045* (2013.01); *A61B 2562/046* (2013.01)

(56) References Cited

U.S. PATENT DOCUMENTS

| | | |
|---|---|---|
| 5,293,867 A | 3/1994 | Oommen |
| 5,689,215 A | 11/1997 | Richardson et al. |
| 6,154,669 A | 11/2000 | Hunter et al. |
| 6,516,218 B1 | 2/2003 | Cheng et al. |
| 6,640,122 B2 | 10/2003 | Manoli et al. |
| 7,367,956 B2 | 5/2008 | King |
| 7,474,918 B2 | 1/2009 | Frantz et al. |
| 7,616,980 B2 | 11/2009 | Meyer |
| 7,941,213 B2 | 5/2011 | Markowitz et al. |
| 8,265,736 B2 | 9/2012 | Sathaye et al. |
| 8,444,559 B2 | 5/2013 | Fink et al. |
| 8,663,121 B2 | 3/2014 | Stickney et al. |
| 9,622,703 B2 | 4/2017 | Badower et al. |
| 9,775,396 B1 | 10/2017 | Olivares Velasco |
| 2009/0088619 A1 | 4/2009 | Turner et al. |
| 2009/0156925 A1 | 6/2009 | Jin et al. |
| 2010/0036275 A1 | 2/2010 | Alkire |
| 2010/0137708 A1 | 6/2010 | Tamura et al. |
| 2011/0130675 A1 | 6/2011 | Bibian et al. |
| 2011/0245707 A1 | 10/2011 | Castle et al. |
| 2012/0022349 A1 | 1/2012 | Poupko et al. |
| 2012/0143020 A1 | 6/2012 | Bordoley et al. |
| 2012/0150011 A1 | 6/2012 | Besio |
| 2012/0226127 A1 | 9/2012 | Asjes et al. |
| 2013/0102872 A1 | 4/2013 | Park |
| 2014/0142410 A1 | 5/2014 | Erb et al. |
| 2014/0243643 A1 | 8/2014 | Sunderland |
| 2014/0257073 A1 | 9/2014 | Machon et al. |
| 2015/0257674 A1* | 9/2015 | Jordan .................. A61B 5/291 |
| | | 600/383 |
| 2015/0282760 A1 | 10/2015 | Badower et al. |
| 2016/0135748 A1 | 5/2016 | Lin et al. |
| 2016/0144186 A1 | 5/2016 | Kaemmerer et al. |
| 2016/0235322 A1 | 8/2016 | Alkire |
| 2016/0287127 A1 | 10/2016 | Kesinger |
| 2016/0346534 A1 | 12/2016 | Isaacson et al. |
| 2017/0055844 A1 | 3/2017 | Umezawa et al. |
| 2017/0112444 A1 | 4/2017 | Lin et al. |
| 2017/0143228 A1 | 5/2017 | Leuthardt, Jr. et al. |
| 2017/0281036 A1 | 10/2017 | Parvizi et al. |

FOREIGN PATENT DOCUMENTS

| | | |
|---|---|---|
| WO | 20140184904 A1 | 11/2014 |
| WO | 2016042499 A1 | 3/2016 |

OTHER PUBLICATIONS

Written Opinion of the International Search Authority for PCT/US2018/042363 dated Oct. 18, 2018.

"Evaluating Major Electrode Types for Idle Biological Signal Measurements for Modern Medical Technology" by Anas Albulbul; Bioengineering Mar. 20, 2016; doi:10.3390/bioengineering3030020; www.mdpi.com/journal/bioengineering.

\* cited by examiner

ELECTRODE ARRAY APPARATUS, NEUROLOGICAL CONDITION DETECTION APPARATUS, AND METHOD OF USING THE SAME

CROSS-REFERENCE TO RELATED APPLICATIONS

The present application is a continuation of U.S. patent application Ser. No. 16/035,781, which claims priority to U.S. Provisional Patent Application Nos. 62/533,738 (filed on Jul. 18, 2017), 62/618,273 (filed on Jan. 17, 2018), and 62/648,559 (filed on Mar. 27, 2018). The entirety of U.S. Provisional Patent Application No. 62/648,559 is incorporated by reference herein.

FIELD

The present innovation relates to a novel device configured to utilize an array of electrodes on the head of a patient for assessing at least one medical condition, electrodes, an array of electrodes, a process and apparatus for facilitating a desired alignment of electrodes on a patient, a process of utilizing an array of electrodes that are positionable on the head of a patient, a process for selecting electrodes of an array of electrodes to utilize for assessing at least one medical condition, and combinations thereof.

BACKGROUND

A fabric headband in which electrodes are in fixed positions can be used to position electrodes on the head of a patient. The electrodes are often intended to be placed so they will fall in the positions described in the 10/20 montage. Other headgear in which electrodes can be included are disclosed in U.S. Patent Application Publication Nos. 2016/0235322 and 2010/0036275. Electrode configurations and uses can also be appreciated from U.S. Patent Application Publication Nos. 2016/0346534, 2016/0287127, 2016/0144186, 2014/0142410, 2014/0243643, 2012/022349, 2011/0245707, and 2010/0137708, and U.S. Pat. Nos. 4,742,831, 5,689,215, 6,516,218, 7,367,956, 7,474,918, 7,616,980, 7,941,213, 8,265,736, 8,444,559, and 8,663,121.

SUMMARY

An apparatus for measuring patient data for use in detection of a neurological condition and methods of making and using the same are provided. In some embodiments of the apparatus, the apparatus can include an electrode array that includes a frame having a plurality of electrode hubs. The frame can be configured to receive a head of a patient so that the patient can wear the frame on the patient's head and electrode members can be positioned on the patient's head so the electrodes are in a desired arrangement on the patient's head when the patient wears the frame. Each of the electrode hubs can have one or more electrode members extending from an outer member or a conductive member for contacting a scalp of the head of the patient. The outer member (or conductive member) can have at least one circuit configured to transmit data received by at least one of the electrode members to a measurement device via a wireless communication connection (e.g. Bluetooth, near field communication, WI-FI connection, etc.) or a wired communication connection. In some embodiments, the outer member or the conductive member is an upper wall of a chamber in which the electrode members are moveable.

Methods of utilizing an array of electrodes and an apparatus for detecting a neurological condition for providing care to a patient are also provided. Embodiments of the method can include manipulation of electrode members or electrode hubs, selection of electrode data for transmission and/or use, and detection of a condition via use of data received from electrode hubs positioned on the head of a patient.

In some embodiments, an apparatus for measuring patient data is provided that includes a frame having a plurality of electrode hubs. The frame is configured to receive a head of a patient. Each of the electrode hubs can have at least one or more electrode members extending from or connected to a housing for contacting a scalp of the head of the patient. The housing can be attached to at least one circuit configured to transmit data received by at least one electrode member to a measurement device. Each hub can be configured such that one of:

(i) Each electrode member is moveably connected to the housing of the hub such that electrode members of the hub are independently moveable from an extended position at which distal ends of the electrode members are contactable with the scalp to a retracted position at which proximal ends of the electrode members are contactable with a conductive member. The electrode members can be moveable within a chamber from the extended position at which the proximal ends are spaced apart from the conductive member to the retracted positions at which the proximal ends contact the conductive member. Each of the electrode members can be moveable independent of the other electrode members.

(ii) Each electrode member is a flexible body comprised of an electrically conductive material extending from the housing to conductively connect the scalp to the hub.

(iii) Each electrode member includes a flexible inner body extending from the housing and an outer covering that coats the inner body. The outer covering can be comprised of an electrically conductive material that extends along the inner body from a distal end of the inner body to a portion of the housing to conductively connect the scalp to the hub.

(iv) Each electrode member has at least one channel defined therein that is in communication with at least one discharge hole defined in the electrode member and is also in fluid communication with a cavity of the housing such that conductive fluid material is passable from the cavity of the housing to emit the conductive fluid material out of the at least one discharge hole along a flow path via the at least one channel.

(v) Each electrode member is configured as a telescoping member having a proximal portion attached to the outer member and a distal portion that is moveable from an extended position to a retracted position in response to pressure applied from the head of the patient when the frame is positioned on the head of the patient. Each of the telescoping members can be moveable independent of the other telescoping members.

Embodiments of the apparatus can include the measurement device being communicatively connectable to the electrode hubs as well as other elements (e.g. a display, an electrode positioning facilitation device, etc.). The measurement device can be configured to select electrode member data received from the electrode hubs to utilize for performing a comparison used to detect whether the patient had a stroke or a seizure.

The conductive member of at least some of the electrode hubs can include a selection circuit that is configured to select electrode member data to transmit to the measurement device. The conductive member can be configured as an outer member that defines the chamber in some embodiments.

Embodiments of the apparatus can include a configuration in which each hub is configured such that each electrode member has the at least one channel defined therein that is in communication with the at least one discharge hole defined in the electrode member and is also in fluid communication with the cavity of the housing such that conductive fluid material is passable from the cavity of the housing to emit the conductive fluid material out of the at least one discharge hole along a flow path via the at least one channel. For such embodiments, the at least one channel can be positioned between an outer surface of the electrode member and a conductor of the electrode member. Each such channel can be defined by a conduit member or other element (e.g. portion of an electrode member, etc.).

Embodiments of a method of detecting a condition of a patient can include positioning a headgear on a head of a patient to align an array of electrodes on the head; selecting electrode members of the array of electrodes to utilize for recording data relating to a body of the patient responding to an evoked potential being passed through the body of the patient or a passive recording of electrical activity of a brain of the patient; collecting data recorded by the selected electrode members and transmitting at least a portion of that data to a measurement device; and the measurement device comparing left-side data from electrode members positioned on a left side of the head to right-side data from electrode members positioned on a right side of the head to determine whether the patient has experienced a stroke or a seizure.

In some embodiments of the method, the positioning of the headgear on the head of the patient can occur such that some electrode members move in response to the head of the patient contacting the electrode members. The electrode members can move such that at least some of the electrode members move into contact with a conductive member of a hub to which the electrode members are attached to form an electrically conducting coupling with the conductive member for transmission of data sensed by the electrode member. Such embodiments of the method can also include passing the evoked potential through the body of the patient.

In some embodiments of the method, the electrode members can move such that at least one of the electrode members of each hub of the electrode members telescopingly retract in response to contact with hair or another object on the head of the patient that prevents a distal end of that electrode member from contacting a scalp of the head of the patient so that other electrode members of the hub are not prevented from contacting the scalp. In some embodiments, the electrode members can flexibly move in response to contact with hair or another object on the head of the patient so that distal ends of the electrode members are passable through the hair or the other object to contact a scalp of the head.

The electrode members can have different structures or configurations. In some embodiments, the electrode members are comprised of an inner body extending from a conductive member and an outer covering, the outer covering comprising an electrically conductive material and the inner body comprised of a polymeric material or elastomeric material.

The selecting of the electrode members of the array of electrodes to utilize for recording data relating to a body of the patient responding to the evoked potential being passed through the body of the patient can include different steps. For instance, such selection can include selecting pairs of corresponding electrode members having a best impedance match prior to passing the evoked potential through the body of the patient or selecting electrode members having a strongest signal after passing the evoked potential through the body of the patient. The selecting of the electrode members can occur via a selection circuit connected to conductive members of the hubs prior to transmitting the collected data to the measurement device. In some embodiments, the measurement device can perform the selecting of the electrode members prior to comparing the left-side data from electrode members positioned on the left side of the head to the right-side data from electrode members positioned on the right side of the head to determine whether the patient has experienced the stroke or the seizure.

The collecting of the data recorded by the selected electrode members can include different collecting steps. For instance, such collecting can include sensing electrical activity of the brain of the patient and recording data relating to the sensed electrical activity of the brain.

Embodiments of the method can include other steps. For instance, embodiments of the method can include actuating a flow of conductive fluid material from a cavity of a housing of at least one hub of electrodes of the headgear such that the conductive fluid material passes out of the cavity, through at least one channel defined in each electrode member attached to the housing and out of at least one discharge hole defined in the electrode member so that the conductive fluid material is emitted out of the at least one discharge hole and flows along a scalp of the patient along a flow path. The actuating of the flow of the conductive fluid material can occur after the headgear is positioned on the head of the patient and prior to the collecting of the data occurring. In yet other embodiments, the conductive fluid can be applied to the patient's scalp or on the electrode members prior to positioning of the headgear on a patient via an injection device. The injection device can be releasably attached to the headgear and removed for such use in response to assessing that at least some of the electrode members or electrode hubs do not have a sufficient connection to the patients' scalp for performing a test on the patient.

A device for the symmetrical placement of electrodes is also provided. The device can include headgear and an array of electrodes attached to the headgear. A first strip can be positioned on an outer top surface of the headgear that extends from a front of the headgear to a rear of the headgear. The first strip can define a centerline indicator. A second strip can be attached to the front of the headgear or the rear of the headgear. The second strip can have a first end positioned adjacent a right side of the headgear and a second end positioned adjacent a left side of the headgear. The second strip can extend linearly and horizontally from the first end of the second strip to the second end of the second strip.

In some embodiments of the device, the second strip can be positioned adjacent the headgear such that the second strip is level as it extends horizontally from the first end of the second strip to the second end of the second strip. A third strip can also be attached to the rear of the headgear so it is on a side of the headgear opposite the second strip (e.g. the front of the headgear if the second strip is attached to the rear of the headgear, the rear of the headgear if the second strip is attached to the front of the headgear, etc.). The third strip can have a first end positioned adjacent a right side of the headgear and a second end positioned adjacent a left side of the headgear. The third strip can extend linearly and horizontally from the first end of the third strip to the second end of the third strip. The first strip can have a first color and the second strip can have a second color that is different from the first color. The third strip, when present, can be a third color that is different from the first and second colors or can also be in the second color.

The first strip and the second strip can have different shapes. For instance, the first strip can have an arc shape and the second strip can be rectangular shaped.

In some embodiments of the device, the second strip can be attached to the headgear such that a midpoint of the second strip is positioned on a front end portion of the first strip or a rear end portion of the first strip. The second strip can be attached to the headgear such that a midpoint of the second strip is positioned to be coincident to a central portion of the headgear and is positioned above a nose of a patient when the headgear is positioned on a head of the patient.

Embodiments of a method for positioning electrodes is also provided that include positioning headgear on a head of a patient so that electrodes attached to the headgear engage the head of the patient when the headgear is on the head of the patient. A first strip can be positioned on an outer top surface of the headgear so that the first strip extends from a front of the headgear to a rear of the headgear. A second strip can be attached to the front of the headgear or the rear of the headgear. The second strip can have a first end positioned adjacent a right side of the headgear and a second end positioned adjacent a left side of the headgear. The second strip can extend linearly and horizontally from the first end of the second strip to the second end of the second strip. The method can also include adjusting the headgear based on how the first strip and the second strip appear to adjust the headgear so that the first strip is centered on a top of the head of the patient.

The second strip can be attached to the headgear such that a midpoint of the second strip is positioned on a front end portion of the first strip or a rear end portion of the first strip. The second strip can also be attached to the headgear such that a midpoint of the second strip is positioned to be coincident to a central portion of the headgear and is positioned above a nose of a patient when the headgear is positioned on a head of the patient. The second strip can be attached to the headgear such that a midpoint of the second strip is aligned with a front end portion of the first strip or a rear end portion of the first strip. The second strip can be level as it extends from its first end to its second end.

The adjusting of the headgear can include multiple different steps. For example, the adjusting of the headgear can include visually inspecting the first strip and the second strip to determine whether the first strip is at a central location on the head of the patient and moving the headgear based on the visual inspection of the first strip and the second strip to center the first strip on the center of the head of the patient. As another example, the adjusting of the headgear can include visually inspecting the first strip and the second strip to determine whether the first strip is at a central location on the head of the patient and, in response to determining that the second strip is off-center such that a midpoint along a length of the second strip is closer to a right side of the patient as compared to a left side of the patient, moving the headgear such that the midpoint is moved closer to the left side of the patient to move the midpoint closer to the central location. As yet another example, the adjusting can also include visually inspecting the first strip and the second strip to determine whether the first strip is at the central location after the headgear is moved to move the midpoint closer to the left side of the patient and, in response to determining that the second strip is off-center such that the midpoint is closer to the left side of the patient as compared to the right side of the patient, moving the headgear so that the midpoint is moved closer to the right side of the patient to move the midpoint closer to the central location.

The second strip can include an indicator at a midpoint of the second strip along a length of the second strip that extends from the first end of the second strip to the second end of the second strip. Embodiments of the method can include using the indicator to identify that the second strip is centrally positioned adjacent a patient's head to confirm the first strip is centrally positioned on the head of the patient. The indicator can be a visible dot, a protuberance on the second strip, or a recess defined in the second strip in some embodiments.

Embodiments of an electronic device are also provided. The electronic device can include a processor connected to non-transitory memory and a housing. The processor and the memory can be within the housing. A representation of a patient head can be defined on the housing with a centerline extending from a first side of the representation of the patient head to a second side of the representation of the patient head. The representation of the patient head can also have a third side between the first side and the second side and a fourth side between the first side and the second side. The fourth side can be opposite the third side. A plurality of first light emitting devices (LEDs) can be positioned on the housing inside the representation of the patient head so that the first LEDs are between the third side of the representation and the centerline. A plurality of second LEDs can be positioned on the housing inside the representation of the patient head so that the second LEDs are between the fourth side of the representation and the centerline.

Each of the first LEDs can be associated with a respective first electrode of a first set of first electrodes that are connectable to the electronic device and each of the second LEDs can be associated with a respective second electrode of a second set of second electrodes connectable to the electronic device. Each of the first LEDs can be illuminatable in a first color in response to a signal that is at a first pre-selected threshold being received from the first electrode of the first set of first electrodes associated with that first LED. Each of the second LEDs can be illuminatable in the first color in response to a signal that is at the first pre-selected threshold being received from the second electrode of the second set of second electrodes associated with that second LED.

Each of the first LEDs can be illuminatable in a second color in response to a signal that is below the first pre-selected threshold and above a second pre-selected threshold being received from the first electrode of the first set of first electrodes associated with that first LED. Each of the second LEDs can also be illuminatable in the second color in response to a signal that is below the first pre-selected threshold and above the second pre-selected threshold being received from the second electrode of the second set of second electrodes associated with that second LED.

Each of the first LEDs can also be illuminatable in a third color in response to a signal that is below the second pre-selected threshold being received from the first electrode of the first set of first electrodes associated with that first LED. Each of the second LEDs can be illuminatable in the third color in response to a signal that is below the second pre-selected threshold being received from the second electrode of the second set of second electrodes associated with that second LED. It should be appreciated that the first color can be different from the second color and also different from the third color and the third color can be different from the second color. In some embodiments, the first color can be green, the second color can be yellow, and the third color can be red. In other embodiments, other colors could be utilized.

An electrode positioning indication map can be positioned on the housing that includes a first line intersected by a second line positioned on the housing to define a plurality of quadrants between the first line and the second line. A plurality of third LEDs can be positioned on the housing along the first line and a plurality of fourth LEDs can be position on the housing along the second line. There can also be a central fifth LED positioned on the housing at a central section at which the first line intersects the second line. There may also be a plurality of quadrant LEDs positioned on the housing in the quadrants.

The third LEDs and fourth LEDs can be are associated with electrodes that are communicatively connectable to the electronic device and are configured to be illuminated to indicate a direction of positional adjustment for the electrodes based on data the device receives from the electrodes. The electrodes can be attached to headgear for positioning on a patient.

Embodiments of the electronic device can include a display connected to the housing. The display can be configured to illustrate an electrode positioning indication map that includes a first line intersected by a second line positioned on the housing to define a plurality of quadrants between the first line and the second line. The display can also be configured to illuminate at least one indicia along the first line of the electrode positioning map and at least one indicia along the second line of the electrode positioning map based on data the device receives from electrodes that are communicatively connectable to the device to indicate a direction of positional adjustment for the electrodes. The display can be configured to illuminate at least one indicia along the first line of the electrode positioning map and at least one indicia along the second line of the electrode positioning map to indicate a direction of positional adjustment for electrodes that are communicatively connectable to the electronic device based on data the device receives from the electrodes.

Embodiments of an electronic device are also provided that includes a housing and a processor connected to non-transitory memory. The processor and the memory can be within the housing. A display can be connected to the housing. The display can be configured to illustrate a visible representation of a patient head with a centerline extending from a first side of the representation of the patient head to a second side of the representation of the patient head. The representation of the patient head can also have a third side between the first side and the second side and a fourth side between the first side and the second side, the fourth side being opposite the third side. The display can be configured to illustrate visible first indicia inside the representation of the patient head between the third side of the representation and the centerline. The display can also be configured to illustrate visible second indicia inside the representation of the patient head so that the second visible indicia is between the fourth side of the representation and the centerline. The display can be configured such that each of the visible first indicia is associated with a respective first electrode of a first set of first electrodes that are connectable to the electronic device and each of the visible second indicia is associated with a respective second electrode of a second set of second electrodes connectable to the electronic device.

Each of the visible first indicia can be illuminable in a first color in response to a signal that is at a first pre-selected threshold being received from the first electrode of the first set of first electrodes associated with that visible first indicia. Each of the visible second indicia can be illuminable in the first color in response to a signal that is at the first pre-selected threshold being received from the second electrode of the second set of second electrodes associated with that visible second indicia. Each of the visible first indicia can be illuminable in a second color in response to a signal that is below the first pre-selected threshold and above a second pre-selected threshold being received from the first electrode of the first set of first electrodes associated with that visible first indicia. Each of the visible second indicia can be illuminable in the second color in response to a signal that is below the first pre-selected threshold and above the second pre-selected threshold being received from the second electrode of the second set of second electrodes associated with that visible second indicia. Each of the visible second indicia can be illuminable in the third color in response to a signal that is below the second pre-selected threshold being received from the second electrode of the second set of second electrodes associated with that visible second indicia. Each of the visible first indicia can be illuminable in the third color in response to a signal that is below the second pre-selected threshold being received from the first electrode of the first set of first electrodes associated with that visible first indicia.

Embodiments of a method of indicating positional adjustment for headgear attached to an array of electrodes are also provided. Such embodiments can include communicatively connecting an electronic device to an array of electrodes attached to headgear. The array of electrodes can include a first set of first electrodes and a second set of second electrodes. The method can also include displaying at least one of:
  (i) an electrode positioning indication map that includes a first line intersected by a second line positioned on the housing to define a plurality of quadrants between the first line and the second line; and
  (ii) a visible representation of a patient head with a centerline extending from a first side of the representation of the patient head to a second side of the representation of the patient head wherein the representation of the patient head also has a third side between the first side and the second side and a fourth side between the first side and the second side where the fourth side is opposite the third side.

In response to data received from the electrodes communicatively connected to the electronic device, illuminating at least one of:
  (a) visible first indicia inside the representation of the patient head between the third side of the representation and the centerline, visible second indicia inside the representation of the patient head between the fourth side of the representation and the centerline wherein each of the visible first indicia is associated with a respective first electrode of the first set of first electrodes and each of the visible second indicia is associated with a respective second electrode of the second set of second electrodes connectable to the electronic device; and
  (b) at least one positional indicia along the first line of the electrode positioning map and at least one positional indicia along the second line of the electrode positioning map to indicate a direction of positional adjustment for the electrodes based on data the device receives from the electrodes that are communicatively connected to the electronic device.

Embodiments of the method can also include adjusting the headgear based on the visible positional indicia and/or adjusting at least one of the electrodes based on at least one of the visible first indicia and the visible second indicia.

The visible first indicia and the visible second indicia can be illuminated such that each of the visible first indicia are illuminated in a first color in response to a signal that is at a first pre-selected threshold being received from the first electrode of the first set of first electrodes associated with that visible first indicia and each of the visible second indicia being illuminable in the first color in response to a signal that is at the first pre-selected threshold being received from the second electrode of the second set of second electrodes associated with that visible second indicia. At least one of the visible first indicia can be illuminated in a second color in response to a signal that is below the first pre-selected threshold and above a second pre-selected threshold being received from the first electrode of the first set of first electrodes associated with that visible first indicia and at least one of the visible second indicia can be illuminated in the second color in response to a signal that is below the first pre-selected threshold and above the second pre-selected threshold being received from the second electrode of the second set of second electrodes associated with that visible second indicia.

The electronic device can receive the data from the electrodes and determine locations at which the positional indicia are to be illuminated along the first line and along the second line for illuminating at least one positional indicia along the first line of the electrode positioning map and at least one positional indicia along the second line of the electrode positioning map to indicate a direction of positional adjustment for the electrodes based on data the device receives from the electrodes that are communicatively connected to the electronic device.

Other details, objects, and advantages of the electrode array, electrode headgear, neurological condition detection device, and methods of making and using the same will become apparent as the following description of certain exemplary embodiments thereof proceeds.

BRIEF DESCRIPTION OF THE DRAWINGS

Exemplary embodiments of headgear, electrodes, electrode arrays, neurological condition detection mechanisms, and methods of making and using the same are shown in the accompanying drawings. It should be understood that like reference numbers used in the drawings may identify like components.

DETAILED DESCRIPTION

Figure 1:
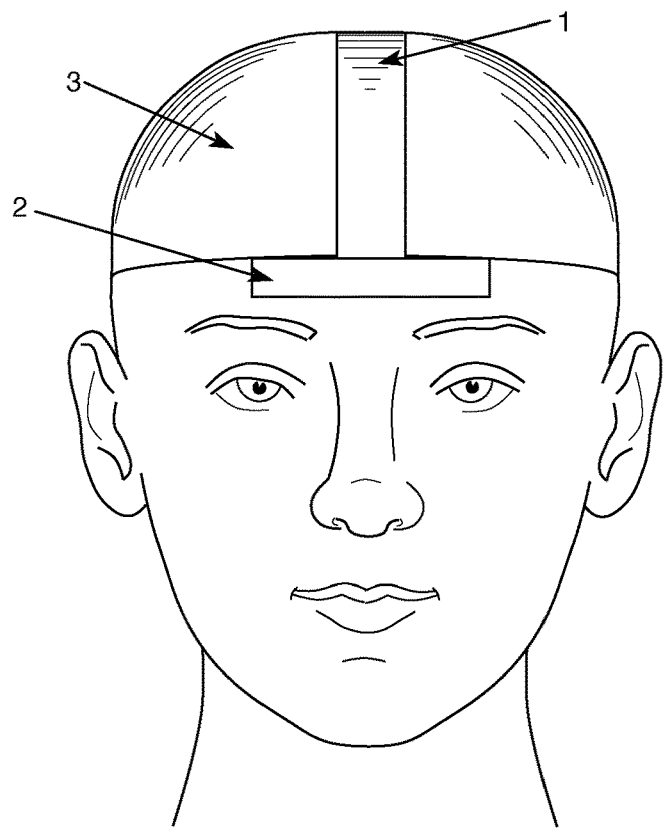
FIG. 1, illustrates a front schematic view of a first exemplary embodiment of the headgear 3. The headgear 3 includes a first strip 1 having a contrasting color to typical hair (e.g. a bright green colored strip, a bright blue colored strip, etc.). This strip may be a colored elongated portion of the headgear itself, or another material affixed to the headgear. It can be referred to as a first indicator strip 1. A second strip 2 is also illustrated as being connected to the headgear 3 and/or the first strip 1. The second strip 2 can be an elongated member that is attached to the first strip so that a length of the second strip extends in a direction that is parallel to the front-to-back direction at which the first strip 1 extends. The second strip can be a contrasting color to typical hair or patient skin color (e.g. bright blue, purple, green, etc.).
Figure 2:
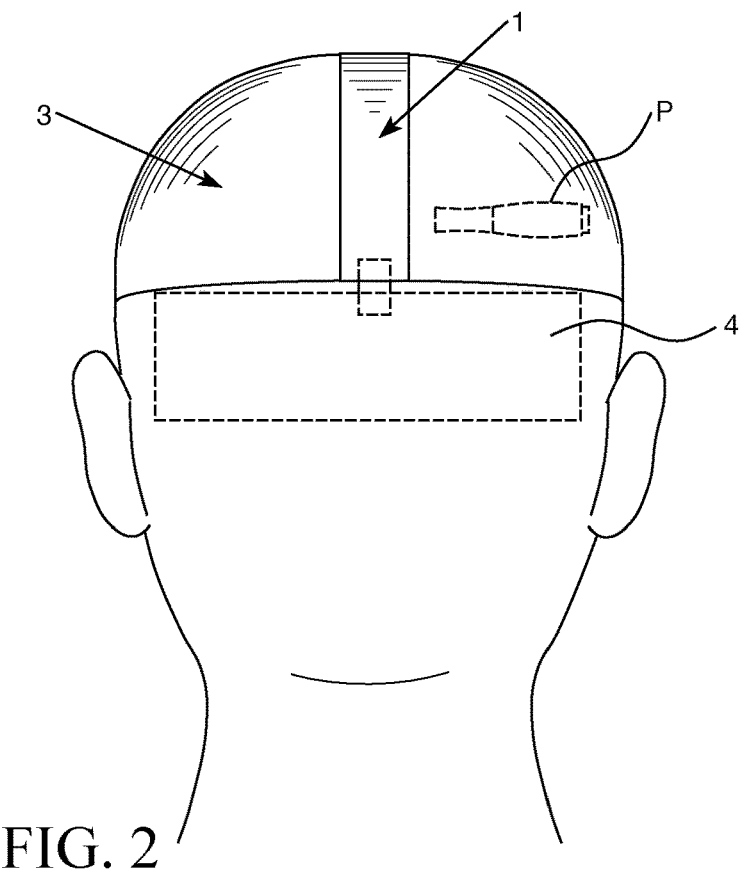
FIG. 2, is a rear schematic view of the first exemplary embodiment of the headgear 3. An array of electrodes can be attached to the headgear (e.g. the electrodes may be sewn into different positions in the headgear or may be attached via connectors that include a plurality of hooks and a plurality of fasteners (e.g. Velcro® material, hook and loop fasteners, clasp mechanisms, etc.) to position the electrodes. The electrodes can be positioned on the inner surface of the headgear so that they are contactable with the head of a patient. The headgear 3 can be configured as any type of headgear such as, for example, a headband, headband frame, a hat, or a helmet.
Figure 3:
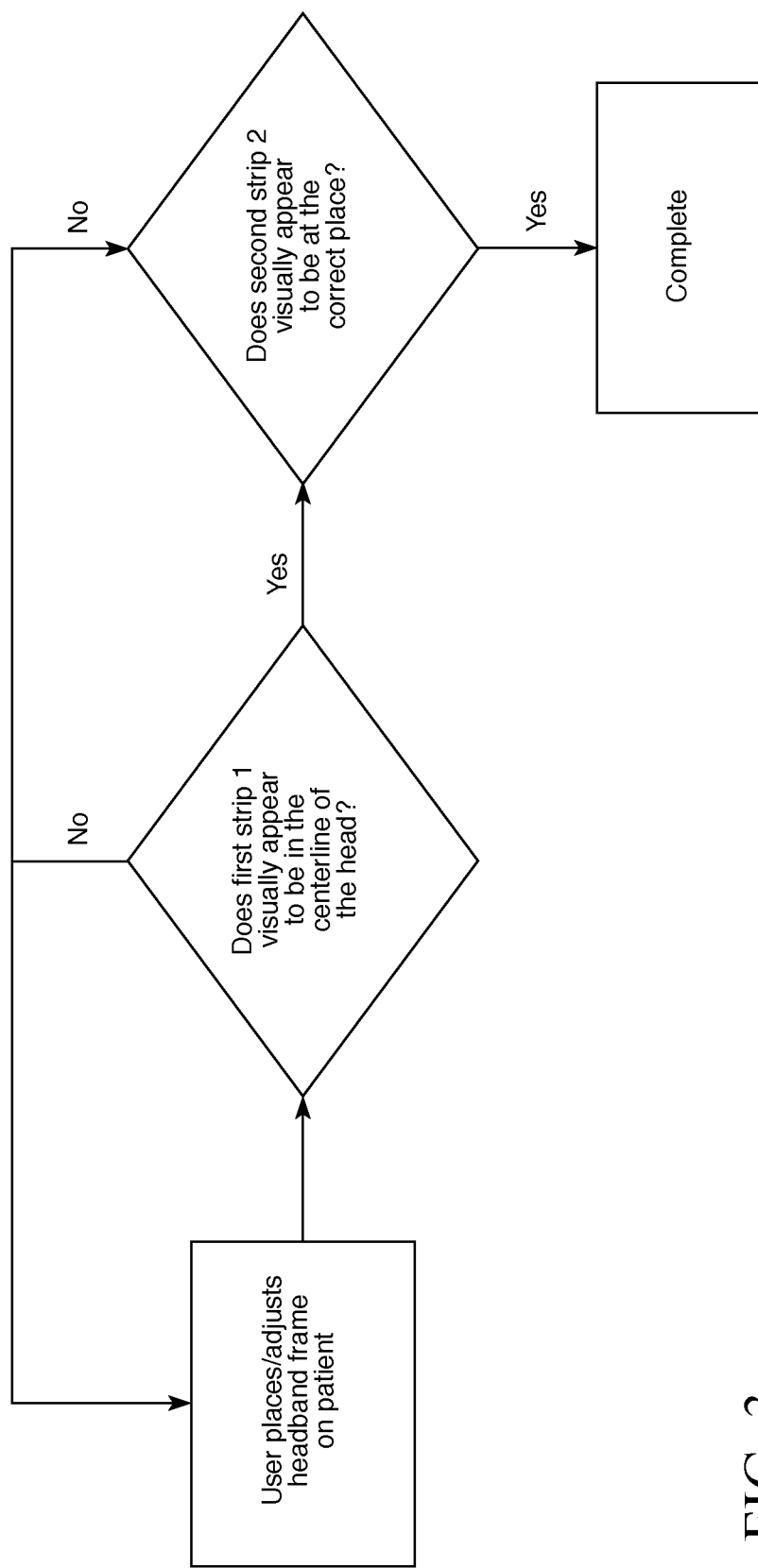
FIG. 3 is a flow chart illustrating an exemplary embodiment of a method for use of an exemplary embodiment of the headgear.
Figure 4:
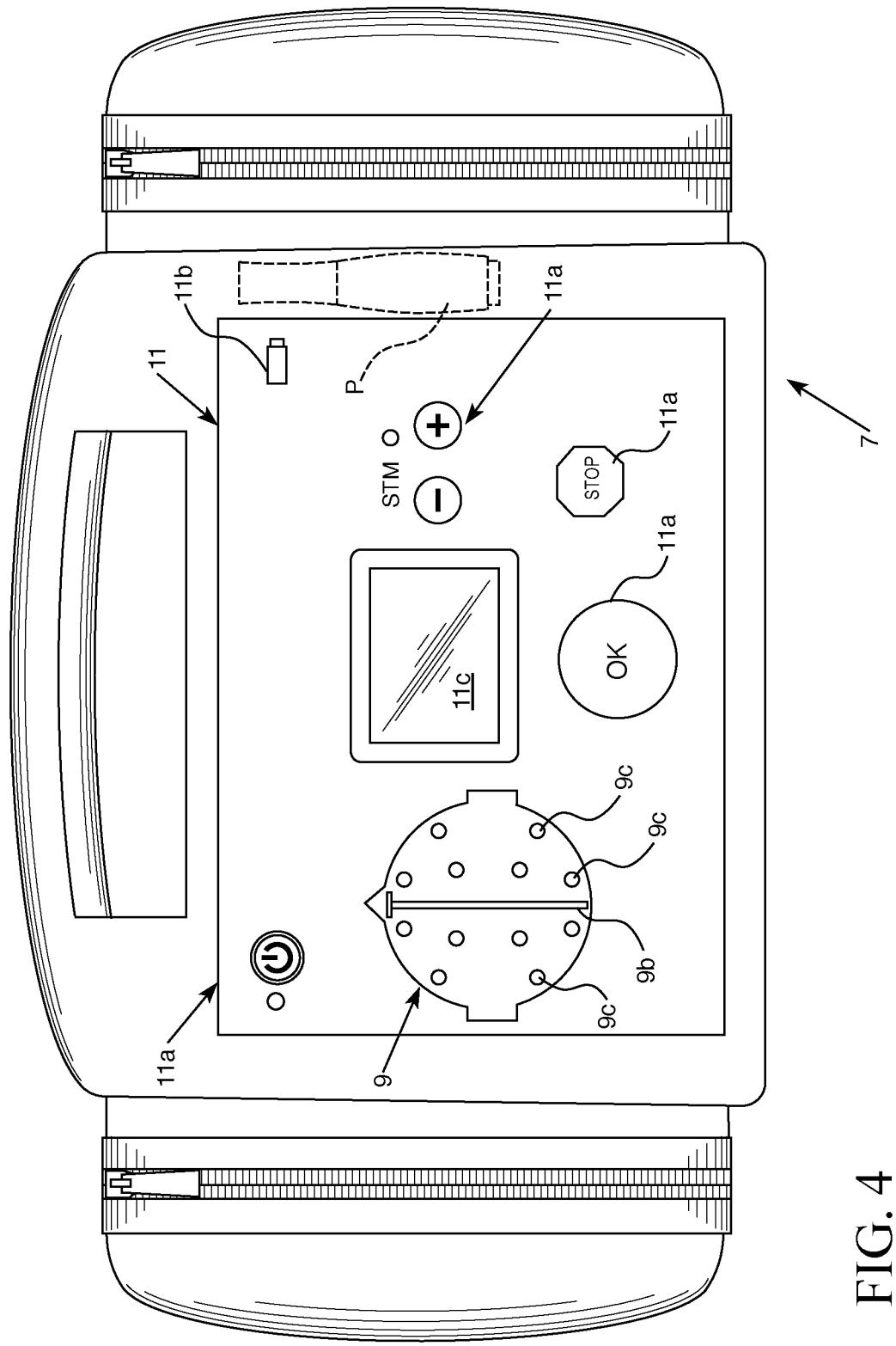
FIG. 4 is a perspective view of an exemplary embodiment of a measurement device to which an embodiment of the headgear can be connected.
Figure 5:
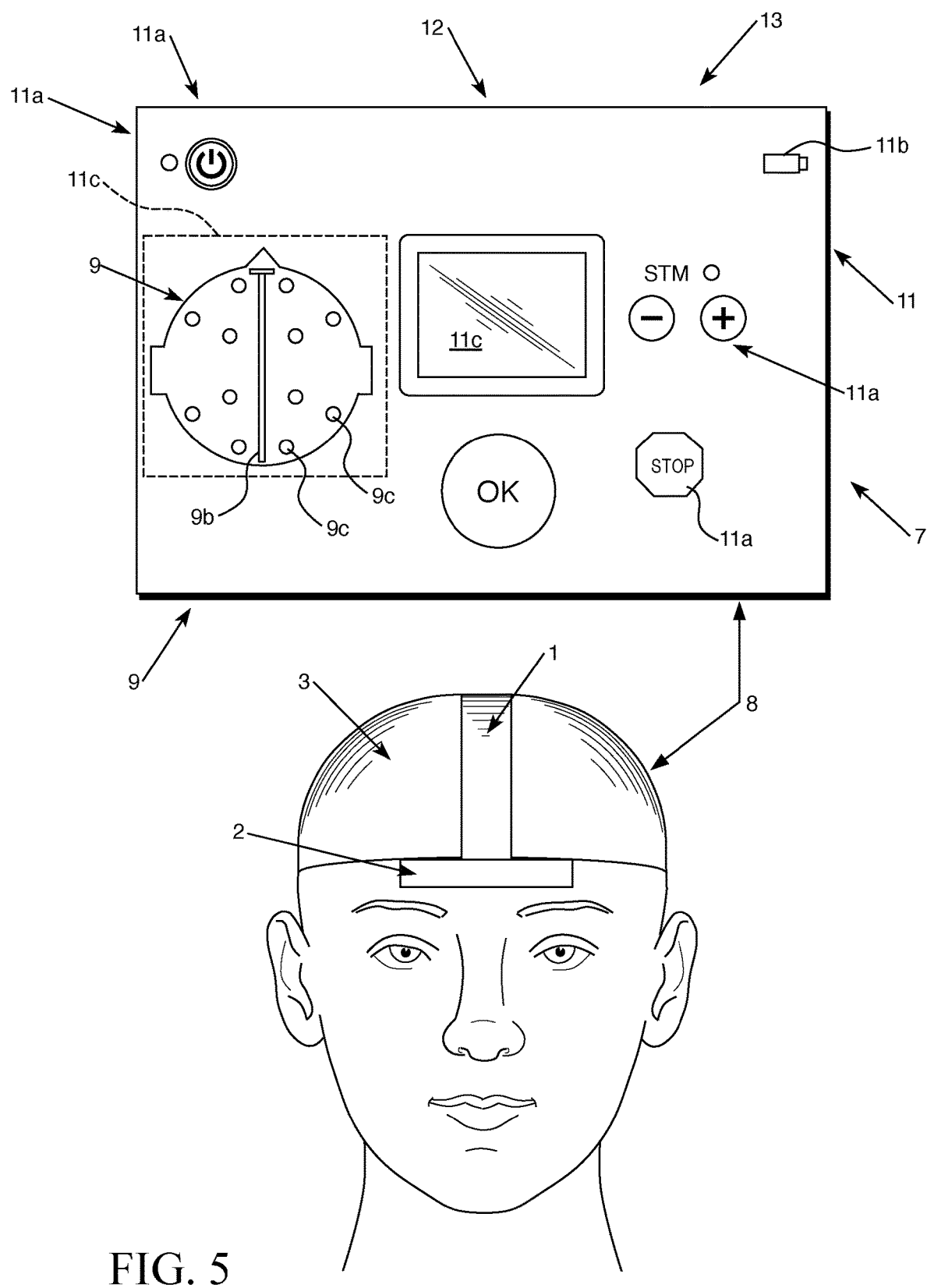
FIG. 5 is a schematic view of an exemplary embodiment of a neurological condition detection apparatus that can include the exemplary embodiment of the measurement device shown in FIG. 4 communicatively connected to the array of electrodes attached to an embodiment of the headgear 3.
Figure 6:
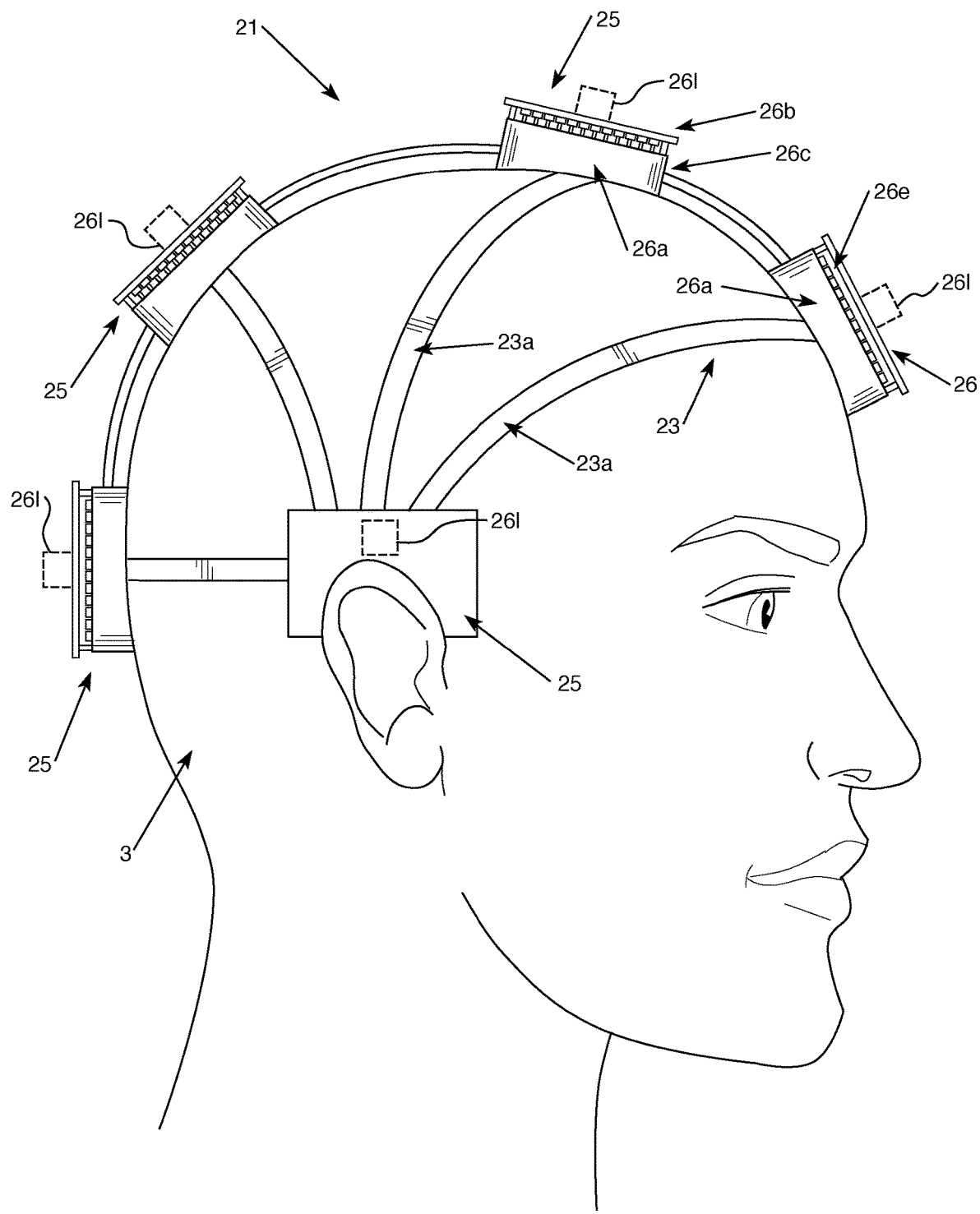
FIG. 6 is a perspective right side view of a second exemplary embodiment of a headgear having an electrode array that is being worn by a patient. An outer covering of the headgear (e.g. shell, fabric covering) is cut away to illustrate the electrode array. The left side view of the embodiment shown in FIG. 6 would be a mirror image of the right side view shown in FIG. 6. It should be understood that in some embodiments, the headgear may not utilize a covering for covering the frame.
Figure 7:
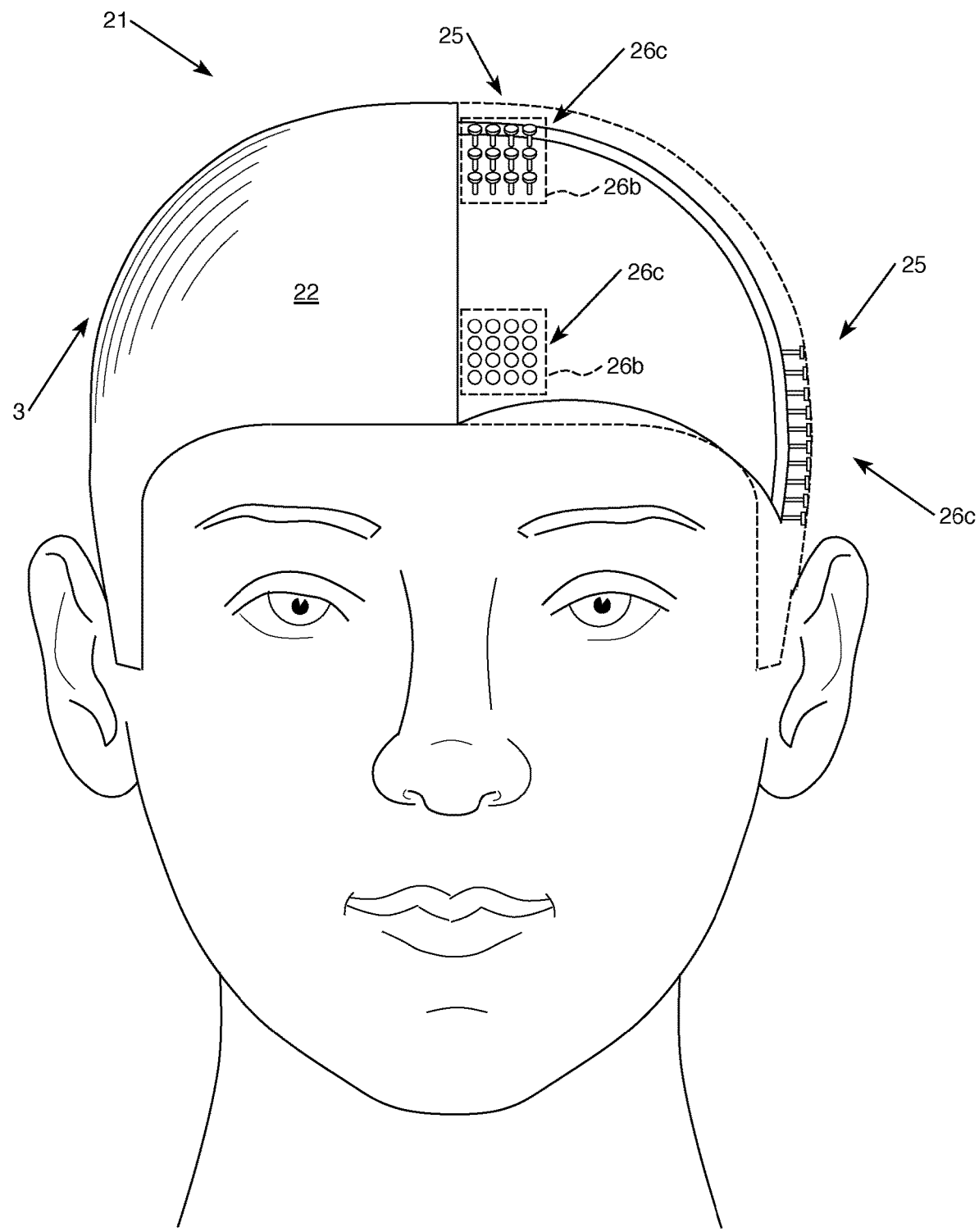
FIG. 7 is a front perspective view of the second exemplary embodiment of the headgear having the electrode array. The left side portion of the headgear outer covering is cut away to schematically illustrate the location of electrodes of the electrode array.
Figure 8:
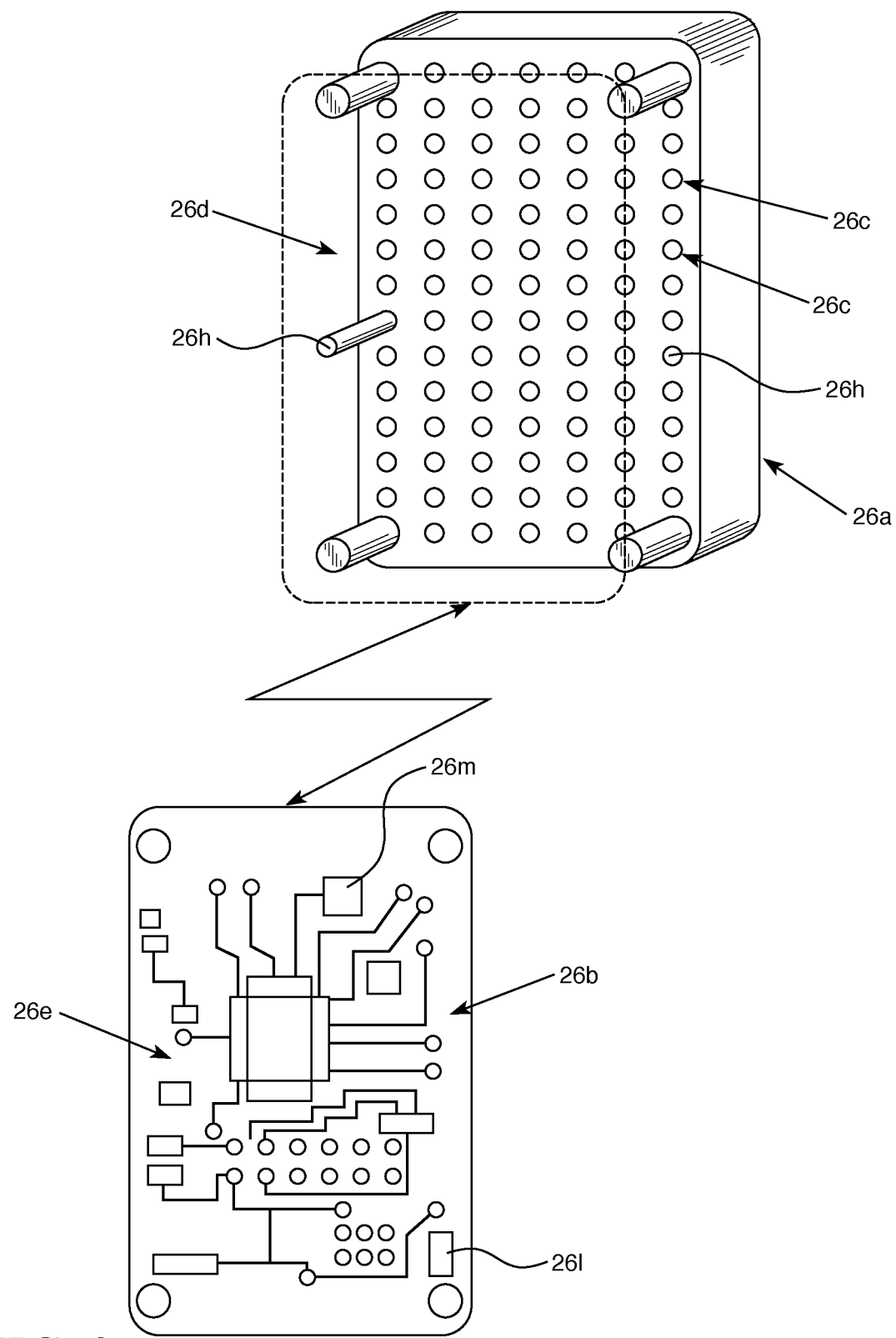
FIG. 8 is an exploded view of an exemplary electrode hub of the electrode array of the second exemplary embodiment of the headgear.

An embodiment of headgear 3 may come in many manifestations ranging from a skull cap to an elastic netting or mesh netting that is sized to be worn on the head of a patient. FIGS. 1 and 2 show the front and rear views of one embodiment of such a headgear 3. The headgear can be configured as any type of headgear such as a type of helmet, a type of elastic netting structure that can be worn on a patient's head, a type of cap, or other type of headgear that can be placed on a patient's head and worn on the patient's head. The headgear 3 can have structure (e.g. a chin strap that can be buckled or otherwise attachable to the headgear 3) and/or other configuration (e.g. elasticity of the headgear structure) to apply a force on the user's head when the headgear 3 is worn on the user's head to ensure a tight fit on the user's head and/or a quality electrical connection. The tight fit can help with electrode placement and positioning, for example.

The headgear 3 can include a first strip 1 that can be arranged to extend from the front to the back of the headgear at a center of the body of the headgear 3 so that the first strip 1 is visible on an external surface of the headgear 3 and is a centerline that extends in a straight manner from the front of the headgear 3 to the back of the headgear 3. When the headgear 3 is worn, the centerline defined by the visible first strip 1 can be considered an arc-type line or a curved line that extends rearwardly from the front of the headgear 3 to the rear of the headgear to define a visible centerline at the center of the patient's head when the patient is wearing the headgear on his or her head.

A second strip 2 can also be provided. The second strip 2 can be configured as an indicator strip that is sized and shaped as a bar, rod, strip of polymeric material, or other type of strip that can be attached to the first strip 1 and/or the body of the headgear 3. The second strip can have a polygonal shape (e.g. rectangular shape, a cubic shape, hexagonal shape, etc.) or other type of shape. The second strip 2 can extend horizontally from adjacent a left side of a patients head to adjacent a right side of the patient's head. The second strip 2 is shown as being at the front of the headgear 3, but it is also contemplated that the second strip 2 could instead be at the rear of the headgear (or that there be a third indicator strip similar to the second strip 2 located at a rear of the headgear 3 so that a user can determine the correct position of the first strip 1 as a centerline via the rear or front views of the patient). The second strip 2 can be rectangular in shape and extend linearly from a left side of the patient to a right side of a patient (e.g. by a left side of the patient's forehead to a right side of the patient's forehead).

The first and second strips 1 and 2 can be connected to a body of the headgear 3. A third strip 4 can also be connected to the body of the headgear 3 in some embodiments. The body of the headgear 3 can be configured to be concave in shape so that it may be worn by a patient on top of the patient's head. The body can be composed of a flexible, but rigid material such as a polymeric material or a plastic material. For instance, the body of the headgear can be a concave shaped body comprised of a polymeric material or a plastic material. Alternatively, the body of the headgear could be composed of mesh or fabric material, an elastic material, or have another type of structure to which the first and second strips 1 and 2 are attachable.

Each of the first and second strips 1 and 2 (and/or third strip 4) can be prominently colored so that a user may look at the strips and the lines defined by those strips (or only one of the strips or lines defined by that strip) when placed on the patient from either the front, back, or top to visually inspect the accuracy of the placement on the electrodes as indicated by the strips and confirmation that the first strip is at a central location on the patient's head to define a centerline corresponding to a center of the patient's head.

The second strip 2 and/or third strip 4 can be used to anchor the headgear 3 so that the headgear 3 stays in its position when worn by a patient. For such an anchoring function, the second strip 2 and/or the third strip 4 can be configured to have a pre-selected weight and have a particular type of structure of connection to the headgear 3 to facilitate such anchoring.

Application for different embodiments may be different depending on the biosignals sought to be obtained by a particular array of electrodes attached to or included within the inner surface of the headgear 3. But, for each embodiment, the headgear 3 can be configured so that the horizontal second strip 2 can be visually placed at the desired location, (e.g. positioned so the center of the second strip 2 is at the midpoint of the forehead of a patient or a center of the forehead of a patient or at a position just above the nose of the patient, etc.). The horizontally extending second strip 2 can extend linearly and be level as it extends from adjacent the left side of a patient's head to adjacent the right side of the patient's head to help a user visibly assess the placement of the headgear 3. A third strip 4, when present, can also be positioned to extend linearly and be level as it extends from adjacent the left side of a patient's head to adjacent the right side of the patient's head to help a user visibly assess the placement of the headgear 3.

As yet another example, the second strip 2 (or a third strip 4 shown in broken line in FIG. 2 when present with the second strip 2 attached to the front of the headgear 3) could be oriented on the back of the neck so that the middle or center of the strip was at a midpoint of the back of the neck or a center of the back of the neck and the strip extend from the left side to the right side of the patient in a linear and level fashion. In yet other embodiments, the second strip 2 could be positioned anywhere in which the second strip 2 extends horizontally so that the second strip 2 extends along its length horizontally and linearly in a direction that is perpendicular to the direction at which the first strip 1 extends from the front of the headgear 3 to the rear of the headgear 3. For instance, the second strip 2 could be placed near the top of the head to extend between the ears of the patient so that the second strip was level as it extended linearly from its first end to its second end.

A user can use the first and second strips 1 and 2 (and also the third strip 4 when present) to help verify that the first strip 1 is properly positioned to define a centerline along a center of a patient's head when the headgear 3 is worn on the patient's head. The second strip 2 and/or third strip 4 can help the user confirm that the first strip 1 is properly aligned to extend from the front of the patient's head to the rear of the patient's head at a center of the patient's head to help ensure the first strip defines a centerline running along a center of the patient's head. Such a positioning can help ensure the array of electrodes are symmetrically positioned on the left and right sides of the patient's head. In this regard, the second strip 2 and/or the third strip 4 may have a visible dot, a recess, a protuberance, or some other visible indicator at its midpoint along its horizontal length that corresponds to the location at which the first strip 1 is positioned to extend from the front to the rear of the headgear to help a user identify that the second strip 2 is centrally positioned for confirmation that the first strip 1 is also centrally positioned to define a centerline along the head of the patient that extends from the front to the back of the patient's head for symmetrical positioning of the electrodes. If a user sees that the second strip 2 or third strip 4 is off-center (e.g. too much to the left or right to be centered), the headgear 3 can be adjusted to center the second strip 2 (and the third strip 4 when present) and first strip 1 so that the midpoint of the second strip 2 is coincident with a center of the headgear 3 and is coincident with a center of the patient's forehead (e.g. above the nose of the patient if the second strip is positioned on the forehead of the patient, etc.). When present, the third strip can also include a midpoint indicator that is positionable to be coincident with a center of the patient's head at the rear of the patient's head.

In some embodiments, the first, second, and third strips 1, 2 and 4 can each be made as part of the headgear material or externally adhered to the headgear 3. The material could be rigid and contoured to conform to the shape of a patient's head or the material could be a soft material or a resilient material that could conform to a patient's head. Each strip can be made of a solid color material or have a particular pre-selected pattern (or both) or some other type of visible indicator feature. In some embodiments, each strip could be configured for low light conditions by also (or alternatively) including light emitting device illuminators (e.g. one or more LED lights attached to each strip to define the centerline (first strip) or horizontal centering indication line (second strip), an LED illumination, or photoluminescent material. A battery, a solar cell, or other power source could be connected to the light emitting device illuminators to power them.

The electrodes attached to the headgear may be in a pre-selected array so that a number of electrodes on a left side of the headgear symmetrically correspond to electrodes on the right side of the headgear (e.g. for each of the electrodes on the left side of the first strip 1, there is a respective left side electrode that symmetrically corresponds to a respective right side electrode so that the corresponding pair of right and left side electrodes are each the same distance away from the centerline defined by the first strip 1 but on opposite corresponding sides of that centerline). The array of electrodes can include a first set of first electrodes that correspond to a first side of the patient's head (e.g. the left side electrodes) and a second set of second electrodes that correspond to a second side of the patient's head on a side of the head that is opposite the first side of the patient's head and on an opposite side of a centerline of the patient's head (e.g. the right side electrodes of the array of electrodes when the first side is the left side or the left side electrodes of the array when the first side is the right side).

The electrodes may be connected to an electronics measurement device 7 via an electrically communicative connection 8 (e.g. a connection via one or more wires, cables, etc. or via a wireless connection by which the measurement device 7 is able to receive a biosignal from the electrodes or data based on the electrode biosignals from electrode hubs 25 of the electrodes).

In some embodiments, the headgear 3 can be utilized in connection with a measurement device 7 that is configured to be a neurological condition detection unit such as the neurological condition detection units disclosed in U.S. patent application Ser. Nos. 15/083,366 and 15/890,493. The electrodes of the headgear 3 can be utilized to facilitate measurements and detection of one or more neurological conditions using such a neurological condition detection unit. The entirety of U.S. patent application Ser. Nos. 15/083,366 and 15/890,493 are incorporated by reference herein.

It should therefore be appreciated that the measurement device 7 can include non-transitory memory, at least one processor, and a power source (e.g. at least one battery). The measurement device 7 can also include a housing 13 that includes at least one graphical electrode map 9 that visibly identifies the electrode array of the headgear 3 and the centerline that extends front to back along the head of a patient that is defined by the first strip 1 and the indicator line to be defined by the left-to-right extending second strip 2. The graphical electrode map 9 can be structured as an outer surface element of a measurement device 7 or can be configured for being displayed on a display 11*c* connected to the measurement device 7 or other computer device (e.g. a communication device, a smart phone, an electrode positioning device, etc.) that can be communicatively connected to the headgear 3 and/or electrode array attached to the headgear 3.

The graphical electrode map 9 can include a representation of a patient head 9*a*. The representation of the patient head 9*a* can be a top view representation of a patient head, for example. The electrode map 9 can also include indicia indicating a center region of the patient head 9*b* (e.g. a centerline, a dashed line of a particular color to indicate the center of the head, etc.). The center region of the patient's head can be identified by the indicia indicating the center region of the patient's head 9*b* can be configured to identify a portion of the representation of the patient head 9*a* that corresponds to a center region of the patient's head extending from the front of the head to the back of the head between the patient's left and right sides) and electrode indicia 9*c* that are positioned in locations on the representation of the patient head 9*a* corresponding to positions at which the electrode hubs of headgear 3 are desired to be positioned. The electrode indicia 9*c* can be LEDs that can be configured to emit light in at least one color (e.g. only green, green and red, or green, red, and yellow, etc.) or the electrode indicia 9*c* can be pre-defined portions of a display configured to have a particular shape (e.g. circle or square shape to be displayed on a graphical display illustrated on a liquid crystal display to represent the electrodes on a representation of the patient head 9*a*, etc.) and also have a particular color to represent each electrode or electrode hub of the headgear 3. The indicia indicating a center region of the patient head 9*b* can also be shown on such a displayed graphic.

For example, each electrode or electrode hub position within the visible map illustrating the representation of the patient's head 9*a* having a first side that may represent the front of the patient's head and a second side that may represent the rear side of the patient's head. A centerline may extend at a center of the representation of the patient's head between the first and second sides of the representation of the patient's head 9*a*. A third side of the representation of the patient's head may extend from the front side to the rear side of the representation of the patient's head and a fourth side of the representation of the patient's head may extend from the front side to the rear side of the representation of the patient's head opposite the third side. The centerline can be positioned between the third and fourth sides (e.g. the third side can be a left side and the fourth side can be a right side or vice versa).

There may be LEDs positioned to represent a corresponding electrode of the array of electrodes (or electrode hub of the array) in the map 9. For instance, there may be a first set of LEDs or other type of first visible indicia that include a respective LED or other type of visible indicia that represents a respective first electrode or first electrode hub of a first set of electrodes positioned on the third side of the patient's head. The first LEDs or other type of first visible indicia (e.g. the first visible indicia can be LEDs or can be other type of visual indicia), can be positioned on the map 9 so that they are positioned between the centerline and the third side of the representation of the patient's head between the first and second sides of the representation of the patient's head 9*a*. There may also be a respective second set of LEDs or other type of second visible indicia that include a respective LED or other type of visible indicia that represents a respective second electrode or second electrode hub of a second set of electrodes positioned on the fourth side of the patient's head. The second LEDs or other type of second visible indicia (e.g. the second visible indicia can be LEDs or can be other type of visual indicia), can be positioned on the map 9 so that they are positioned between the centerline and the fourth side of the representation of the patient's head between the first and second sides of the representation of the patient's head 9*a*.

When the electrodes are not properly positioned for obtaining a signal from a patient, the LEDs may emit a red color (or other first color) to indicate no signal is obtainable from that electrode. If the electrode is able to provide a sufficiently strong signal, the LED may emit a green color (or other second color) to indicate the electrode is properly positioned. If the electrode is positioned so that the measurement device 7 is able to receive a signal from the electrode, but the signal strength is below a pre-selected threshold level, the LED for that electrode may emit a yellow color (or other third color) to indicate a weak signal so that a user can re-assess the headgear or electrode on the patient to determine why the signal is weak prior to a measurement being performed. Key indicia (e.g. display of a key) can be provided near the map 9 to identify how a particular color corresponds to the electrode position or electrode ability to obtain a biosignal from the patient for the multiple different colors that each LED may emit. The graphical map with the LEDs on the external surface of the housing of the measurement device 7 can provide a visible indicator to help a user confirm the electrodes are properly positioned on a patient via the headgear 3 for obtaining biosignal measurements before a measurement is taken.

In the event a user sees that one or more of the LEDs is red or yellow, the user can take action to adjust the electrode positioning on the patient until those electrodes are better positioned for recording biosignals and the LEDs corresponding to those electrodes are displayed in the second color, or at least the third color e.g. all the electrode representing LEDs are green or are either green or yellow in illumination to indicate that a signal is receivable at each electrode of the electrode array). Once an acceptable position for all the electrodes is determined from the map 9, the measurement device may be actuated so that the patient experiences an induced voltage (e.g. "a shock") and the electrodes can be used to measure the patient's response to that event for assessing a neurological condition of the patient. The user can also utilize the presence of some LEDs being in a yellow color or other third color to assess the results in context of the relative electrode connectivity issues to help interpret the reliability of the measurement information obtained via the measurement device 7 and electrodes or assess whether the patient should immediately undergo another measurement or evaluation using the measurement device 7.

In some embodiments, a first pre-selected threshold can define a good electrically conductive connection between an electrode hub 25 and a patient that can be used for actuation of the displayed color for electrode indicia 9c (e.g. determining whether the electrode indicia 9c should be illuminated in a green or yellow color). The first pre-selected threshold value can be an electrical conductivity resistance threshold that is 5,000 ohms or a value in the range of 2,500 ohms to 10,000 ohms. If the value is at or under the first pre-selected threshold value, the electrode indicia 9c can be displayed the first color (e.g. green) and if the value is over the threshold, the electrode indicia 9c can be illuminated in a second color (e.g. yellow). A second pre-selected threshold can be used for determining whether the electrode indicia 9c should be illuminated in the second color (e.g. yellow) or the third color (e.g. red). An electrical conductivity resistance threshold of 30,000 ohms or a value in the range of 15,000 ohms to 40,000 ohms could be used for such a second threshold value. Of course, other values could alternatively be selected for the first and second pre-selected thresholds to account for a particular type of electrode configuration or to meet a particular set of design criteria. In yet other embodiments, the threshold may be a value that is in another unit of measure (e.g. volts or amps). The unit of measure that is utilized for the threshold detection values can be based on the type of sensor or detection methodology utilized for assessing the electrically conductive connection between an electrode member 26c and the patient's scalp 30.

The representation of the patient's head 9a and the graphical map 9 defined on a housing that utilizes this representation, LEDs and a centerline can also be defined by code stored in non-transitory memory that is processed by a processor so that a display 11c displays a graphic on the display 11c that illustrates such a representation. In such a representation, the LEDs may be replaced by the display illuminating portions of the display 11c that are to be representative of the electrodes. The illumination of that indicia can be in a different colors to indicate a different level of connectivity (e.g. a first color to represent a good position and connection, a second color to represent a weak connection, or a third color that represents a position that results in no signal being received, etc.).

Figure 27:
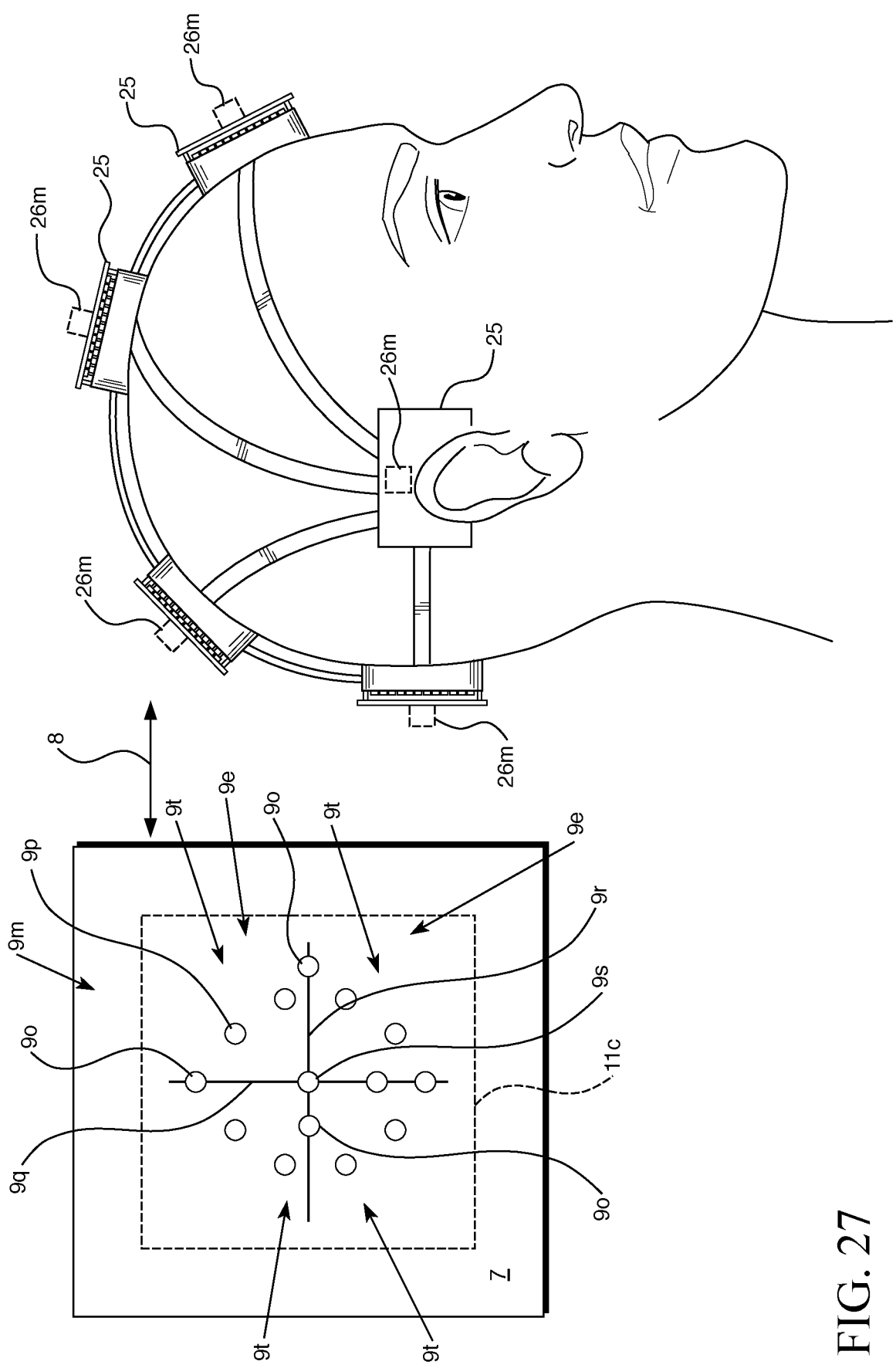
FIG. 27 is a schematic view of an exemplary embodiment of the headgear communicatively connected to an exemplary computer device (e.g. a measurement device 7 or other type of electronic device including a display 11c (e.g. a liquid crystal display, a monitor, etc.) illustrating an exemplary electrode hub positioning display that is providable for facilitating headgear positional adjustment to help a user try to optimize electrode hub placement on a patient prior to a test (e.g. measurement, evaluation, etc.) of the patient being conducted via a measurement device 7 and electrode array.

Referring to FIG. 27, there may also be other displays related to electrode array positioning that may be displayable to a user. Such displays can be provided in addition to the use of the graphical map 9. In other embodiments, such displays can be provided as an alternative to the use of the graphical map 9.

For instance, a display 11c of the measurement device 7 or a display of an electrode position assistant device can be configured to be communicatively connected to the electrode array that includes a number of electrode hubs 25 to communicate with the headgear 3, the array of electrodes and/or the electrode hubs 25 of the array to facilitate illustrating a displayed representation for indicating how the headgear 3 should be adjusted to improve the positioning of the headgear 3 and electrode array on the patient's head prior to a measurement being performed via a measurement device 7. The electrode hubs can include a first set of first electrode hubs in which each of the first electrode hubs is to be positioned on a left side of the patient's head and a second set of second electrode hubs in which each of the second electrode hubs is to be positioned on the second side of the patient's head. The first side of the patient's head can be a right side of the patient's head and the second side can be the left side of the patient's head or vice versa. It should be understood that if the front and rear sides of a patient's head are considered to be the first side and the second side of the patient's head, then (i) the left side of the patient's head can be considered the third side and the right side of the patient's head can be considered the fourth side or (ii) the right side of the patient's head can be considered the third side and the left side of the patient's head can be considered the fourth side The displayed representation that is displayable via the display 11c or is definable on a housing of an electronic device (e.g. housing of measurement device 7 etc.) can be a positioning indication map 9m. For instance, the positioning indication map 9m can be defined on a housing of the measurement device 7 or an electrode position assistant device and have visible indicia positioned thereon (e.g. LEDs, lines, other indicia) to provide the positioning indication map 9m. As another example, the positioning indication map 9m can be configured to be displayed via a display 11c of an electronic device such as the measurement device 7 or an electrode position assistant device.

The positioning indication map 9m can include a vertical line 9q and a horizontal line 9r that intersect each other to define a cross or a "+" type shape. Illuminable indicia (which can also be considered visible indicia) 90 can be positioned on these lines or displayable on these lines. Illuminable indicia 9p can also be positioned or displayable in the quadrants 9t defined by the cross shape. The illuminable indicia can be LEDs, other type of light emitting device in pre-selected regions in the map positioned on a surface of a housing, or be defined to be colored regions on a display 11c corresponding to such locations. Other indicia can include names or symbols (e.g. "Front", the letter "F", etc.) near or at a terminal end of each line to identify the regions of the cross shape defined by the vertical and horizontal lines 9q and 9r as corresponding to the front, rear, left, and right sides of a patient's head.

The positioning indication map 9m can be configured so that when the headgear 3 is properly positioned on a patient's head to properly align the electrode array on a patient's head, the center section 9s of the cross-shape or "+" shape is illuminated via a light emitting diode or a portion of the display causing that region of the display at the center section 9s of a displayed cross "+" to be illuminated in a pre-selected way (e.g. a particular color and/or shape etc.). For example, there may be an illuminated circle or dot that is illuminated in a pre-selected color (e.g. green or blue) at the intersection of the cross ("+") of the positioning indicia map 9m. Other proper positioning indicia can be provided as well (or as an alternative to illumination of an indicia at center section 9s), such as all the LEDs on the vertical and horizontal lines being lit in a pre-selectee color (e.g. green or blue, etc.) or the display 11c displaying the vertical and horizontal lines 9q and 9r in a pre-selected color to indicate acceptable positioning.

In the event the headgear 3 and electrode array is not properly positioned, one or more indicia may be displayed to a user on the positioning indicia map 9m to indicate an adjustment of the headgear 3 is needed to properly position the headgear 3 and electrode array on the patient's head. For configurations in which the positional indication map 9m is illustrated on a display 11c, direction arrows may be displayed to indicate a positional adjustment direction about which headgear is to be moved to improve the position of the electrodes (or electrode hubs 25) of the headgear 3 on the patient. Such arrows could alternatively be pre-defined on a housing and illuminated when the arrow indication is determined to be appropriate for displaying a positional adjustment indicator based on electrode data received from the electrode array.

As another example, LEDs can be configured to emit a color in a second pre-selected color or a third pre-selected color (e.g. red or yellow) at spaced positions on the vertical and/or horizontal lines 9q and 9r to indicate a degree to which the headgear 3 needs adjusted forwardly (or backwardly) and sidewardly (e.g. to the left or to the right). Such a motion can correspond to a rotational type adjustment motion or discreet linear motions (e.g. sideward adjustment motion followed by a forward or rearward adjustment motion).

For example, colored lighting or other indicia may be configured to be displayed on a left side of the horizontal line 9r to indicate that the headgear needs adjusted to the left to a certain degree. The farther away from the center section 9s the colored light appears can correspond to the greater degree to which sideward motion is needed to properly position the headgear 3. As another example, colored lighting can be emitted on the vertical line above or below the center section 9s to indicate a degree to which the headgear 3 needs adjusted forwardly or backwardly). As yet another example, colored lighting can be emitted in the second or third color on the horizontal line 9r and the vertical line 9q to indicate a sideward adjustment motion and a forward or backward adjustment motion is needed. The distance between the center section 9s (e.g. central intersection of the cross "+" shape) and the emitted light in the second or third color can indicate the extent to which an adjustment is needed (e.g. the farther away a light is from the center section 9s, the more motion in that direction is needed).

The color of the light emitted to indicate an adjustment is needed can be in the second color to indicate a level of the conductive connection the electrodes have to the patient's scalp in the particular position. Coloration in the second color (e.g. yellow) can indicate the contact is acceptable and coloration in the third color can indicate that the contact is not acceptable. Alternatively, the color can further identify the extent to which the adjustment motion must be made (e.g. a yellow color as the second color a certain distance away may indicate a first distance of adjustment motion and a red color as the third color can indicate a further second distance of adjustment motion is needed).

Indicia in one or more quadrants 9t can also be emitted when the position is not proper. The light emission in the quadrants can be used to indicate that a rotation of the headgear is needed to adjust the position of the headgear on a patient to properly align the electrode array on the patient's head. For example, a light can be emitted in a quadrant between the top end of the vertical line 9q and the left side end of the horizontal line 9r to indicate that a clockwise rotation or a counterclockwise rotation to a particular degree (e.g. 15 degrees or 20 degrees, etc.) is needed to adjust the position of the headgear on the patient's head to properly align the electrode array. Light emitted in the opposite quadrant between the top end of the vertical line 9q and the right side end of the horizontal line 9r can indicate an opposite rotational adjustment motion is needed (e.g. a clockwise rotation). In other embodiments, the rotational indication provided by such indicia can be reversed (e.g. an indication of a clockwise rotation can be provided by light emitted in a quadrant between the top end of the vertical line 9q and the left side end of the horizontal line 9r and a counterclockwise adjustment rotation can be indicated by light emitted in a quadrant between the top end of the vertical line 9q and the right side end of the horizontal line 9r).

A visible key or other instructions can be provided to help a user correlate the indicia displayed for positional adjustment with how to move the headgear 3 on the patient based on the displayed indicia. A user can utilize such instructional information for learning how to utilize the indicia for improving the positioning of the headgear 3 on the patient prior to any testing being performed.

The positional information conveyed to the measurement device 7 (or a separate electrode position assistant device) to provide electrode positioning information can be from sensors attached to the electrodes or the electrode hubs 25 of the headgear 3. For example, such information can be conveyed by measurement data obtained by one or more electrode positioning sensors 26m, which can be configured as gyroscopes or accelerometers in some embodiments. There may be at least one electrode positioning sensor 26m included in each electrode hub 25 of the electrode array included in the headgear 3 and subsequently communicated to the measurement device 7 (or a separate electrode position assistant device). Such data can be conveyed along with data from the electrode members 26c and/or electrode hubs 25 indicating a signal quality of the connection electrode members have with the patient's skin for generation of one or more maps (e.g. geographical map 9 and/or positioning indication map 9m). The device receiving that measurement data may then respond to that data by providing the positioning indication map 9m via the display 11c based on that received data or by actuating different lights or other indicia for the positioning indication map 9m positioned on the housing of the device. Lighting or other indicia for the geographical map 9 can also be actuated based on that data. Code stored in non-transitory memory that is accessible to a processor of the measurement device 7 can define how the data from the gyroscopes is used to actuate indicia on the positioning indication map 9m positioned on a housing or generate the positioning indication map 9m on a display 11c having different indicia illuminated or otherwise displayed. Code stored in the non-transitory memory that is accessible to the processor of the measurement device 7 can also define how the data from the electrode members 26c and/or electrode hubs 25 can actuate indicia being displayed on the graphical map 9 (e.g. light coloration of LED lights, etc.).

For embodiments that utilize both a positional indication map 9m and a graphical map utilizing a representation of a patient's head 9a, and both representations are defined on a housing of a device, the housing may be considered to have many different sets of LEDs or other types of visible indicia. For instance, there may be first and second LEDs on the representation of the patient's head that are part of first and second sets of LEDs that are to correspond to respective electrodes or electrode hubs as discussed herein. LEDs along vertical and horizontal lines and/or in quadrants can be additional LEDs or sets of LEDs (e.g. can be considered third LEDs, fourth LEDs, fifth LEDs etc.) and when a central LED is positioned at the intersection of the cross or "+" shape of the intersecting lines of the positional indication map 9m, that LED can be considered yet another LED of a set of at least one LED (e.g. a third LED, a fourth LED, fifth LED or a sixth LED depending on how other LEDs on the housing are positioned or present and how one references the different sets of LEDs). In yet other embodiments, one of the positional indication map 9m and the graphical map utilizing a representation of a patient's head 9a, can be defined on a housing of a device and the other of those two representations can be displayable via the display 11c (e.g. (i) the housing of the measurement device 7 has the representation of the patient's head 9a defined thereon and the display 11c displays the positional indication map 9m or (ii) the display 11c displays the patient's head 9a representation and the housing of the measurement device 7 defines the positional indication map 9m).

It should be appreciated that the measurement device 7 can include a number of input mechanisms 11, output mechanisms 12 and/or input/output mechanisms (also referred to as I/O mechanisms). For instance, the measurement device can include a number of buttons 11a (e.g. a power button, a start button, a stop button, etc.), an indicator to indicate battery life 11b, and a display 11c (e.g. a liquid crystal display). The display 11c could be a touch screen display or another type of display. A printer can also be communicatively connected to the measurement device 7 for printing out data received by the measurement device 7 or assessment results the measurement device 7 can provide based on biosignal data received from the electrode array of the headgear 3. The measurement device 7 can also be configured to provide measurement data from the measurements taken via the electrodes obtained via a communication connection 8 to at least one other device (e.g. a computer, a tablet, a server, a printer, etc.).

It should be appreciated that different embodiments of the headgear 3 having an electrode array and measurement device 7 can utilize different arrangements to meet a particular set of design criteria. For instance, the geometry, height, width (or diameter) of each headgear can be sized to meet a particular design objective (e.g. account for certain type of material to be used for forming the headgear (e.g. fabric, threading, etc.). As another example, the number of electrodes in the array of electrodes and their positioning in the headgear or on the headgear can depend on a particular set of design criteria. As yet another example, the size and shape of the first and second strips 1 and 2 and the number of such strips that are used can be any of a number of different geometries and shapes to meet a particular set of design criteria. As yet another example, the type of graphical map, the color at which LEDs could be colored to indicate an electrode property, the shape of the housing, or the type of input and/or output mechanisms used for the measurement device, and the configuration of the positioning indication map 9m can be any of a number of arrangements to meet a desired design objective or a set of design criteria.

Referring to FIGS. 6-8 and 14-26, other embodiments of the headgear 3 can be appreciated. In the embodiment of FIGS. 6-8 and 14-26, the headgear structure 21 can be configured as a helmet or other type of headgear structure that has a frame 23 that includes a plurality of interconnected straps 23a. The straps 23a can be composite straps, elastomeric straps, polymeric straps or be a fabric-based set of straps 23a (or combinations of such straps). Each strap 23a can be attached to multiple other straps or at least one other strap or the straps can be defined in a molded or otherwise fabricated shaped headgear (e.g. plastic injection molded, sewn frame, etc.). In yet other embodiments, the headgear 3 can have another type of frame structure.

A plurality of electrode hubs 25 can be attached to the straps 23a. Each hub 25 can be positioned so that it is in a pre-selected location on the frame 23 so that there are at least two sets of corresponding electrode hubs 25—a first side (e.g. a "left side") set of electrode hubs and a second set (e.g. a "right side" set) of electrode hubs 25. The electrode hubs 25 of the first side set are positioned so that each one of the first side set of electrode hubs 25 is in a position that corresponds to a position of a respective corresponding electrode in the second side set of electrode hubs 25. These positions can include a first forward position to be positioned by a patient's forehead when the frame 23 is on a patient's head, a rearmost position to be positioned by a patient's back of the head, and at least one intermediate position between the forward and rearward positions. There can also be an ear-adjacent position for electrode hubs 25 of the first and second sets. The ear-adjacent positioned electrode hub of the first side set can be adjacent a user's left ear, for example, and the electrode hub 25 of the second side set that is the respective corresponding electrode hub for this electrode hub 25 can be an electrode hub 25 of the second side set positioned adjacent a user's right ear. The first and second sets of electrode hubs 25 are positioned so that the electrode hubs 25 in the first side set can be considered a mirror image of the second side set so that the first side set electrode hubs 25 and second side set electrode hubs 25 are positioned at the same or substantially the same positions on opposite sides of a patient's head.

Each of the first and second sets of hubs 25 can be arranged so that the mirror image located hubs form a pair of hubs (e.g. the left side hub by the patient's left side ear and the mirror image right side hub by the patient's right side ear can be a first pair of corresponding left and right side electrode hubs 25, a front most hub on the left side of the patient's head and a front most hub on the right side of the patient's head can be a second pair, a rear most hub on the left side of the patient's head and a rear most hub on the right side of the patient's head can be a third pair, etc.). The pairs of hubs 25 can be utilized for evaluating which electrode hubs are to be utilized for collection of measurement data and for use in receiving measurement data from one or more electrode members 26c of each hub for the measurement device 7 to perform a comparison of the left and right side data from the pair to evaluate differences in how the patient's body responded to an evoked potential that is passed through the patient's body by an evoke electrode or other mechanism. The use of the pairs of data for multiple pairs of left and right side electrode hubs can be utilized for such a comparison. Each of the hubs 25 can also be configured to determine which of the electrode members 26c of the hub 25 should be used for collecting data from a patient (e.g. biosignal data from the patient's body responding to an evoke event, or shock, conveyed to the patient body via the measurement device 7), or determining which data from which electrode members 26c of the hub 25 are to be transmitted to the measurement device 7.

Each electrode hub 25 can include a hub body 26 that includes an outer member 26b, a housing 26a that is configured to be positioned between the patient's head (when the headgear 3 is worn) and the outer member 26b, and a plurality of electrode members 26c that are moveably positionable within a chamber 26d defined by the outer member 26b and the housing 26a. The outer member 26b can be a conductive member that is comprised of a conductive material. The outer member 26b can define an outer side of the chamber 26d in which the electrode members 26c are moveably positionable. The outer member 26b can include a circuit board having at least one circuit 26e positioned thereon. The at least one circuit 26e can at least include a transmission circuitry for communicatively connecting electrode members 26c that contact the outer member 26b with the measurement device 7 so that at least some (or all) of the measurement data sensed by the electrodes that contact the outer member 26b can be communicatively transmitted to the measurement device 7. The transmission circuitry can be configured so that data collected by electrode members 26c via a particular hub has an identifier included with the data transmitted to the measurement device 7 so that the measurement device can store the electrode data in a database or other data store and organize that data. The identifier can identify where the electrode hub 25 is located on the patient's head (e.g. a particular pre-selected location that the hub is to be positioned on a head when the headgear 3 is worn properly for an evaluation measurement). The identifier can also be configured to positionally identify the electrode member 26c of the hub 25 to positionally identify the location of the electrode members 26c of the hub 25 for the electrode member 26c data being transmitted from the hub 25 to the measurement device 7. The measurement device 7 can be configured to utilize the transmitted location data to properly map the data from corresponding right and left side pairs of electrodes for subsequent use in comparing right and left side passive EEG or comparing right and left side body responses to an evoke event (e.g. a "shock") used to collect the data from the patient's body to evaluate a condition of the patient.

In some embodiments, the at least one circuit 26e can include an electrode transmission selector circuit that is configured to select the electrode data received from a particular electrode member 26c for sending to the measurement device 7. For instance, only the electrode data that has the strongest signal can be selected for transmission. In other embodiments, the at least one circuit 26e may not include such a selector mechanism and all electrode data from all the electrode members 26c that contact the outer member 26b can be transmittable to the measurement device 7.

The electrode members 26c can be positioned in the housing 26a so that they are moveable from an initial position to a retracted position. In their initial positions, the electrode members 26c can extend out of the housing for contacting a patient's head when the patient is wearing the headgear 3. The force exerted to have the headgear 3 worn on the patient's head and fit thereon can function to also apply a force via the patient's head against the distal ends 26g of the electrode members 26c to drive the electrode members 26c to move to a retracted position in which their proximal ends 26h opposite their distal ends 26g pass through the chamber 26d towards the outer member 26b. Electrode members 26b that get caught up in patient hair or an article of clothing (e.g. a hair pin, a ribbon, etc.) may stop retracting to its fully retracted position. But, other electrode members 26c may be forced by their distal ends' contact on a patient's scalp 30 to fully retract so their opposite proximal ends contact the outer member 26b. The contact of the outer member 26b can be configured to provide an electrically conducive connection between the electrode member 26c and the outer member 26b. For example, the electrode member 26c can have a metal body (e.g. a copper body, a gold body, etc.) or a metallic outer coating over the body of the electrode member 26c so that contact with a metal layer of the outer member 26b that defines a sidewall of the chamber 26d is conductively coupled upon the electrode member proximal end contacting the outer member 26b.

Configurations in which a proximal end 26h of the electrode members 26c contact the outer member 26b for forming a communicative connection to the outer member 26b can permit electrode hubs 25 to be formed without the need for wires to communicatively connect the electrode members 26c to the hubs 25. Wires also can be avoided for hubs 25 to communicatively connect to the measurement device 7 as each hub can have a transmission circuit that is configured to provide a wireless communication transmission (e.g. near field communication connection, Bluetooth communication connection, short wave radio communication connection, etc.). The non-inclusion of wires can also provide improved precision and/or accuracy to collected data by decreasing artifacts of the data that can be present when wires are utilized in conducting signals for communication of data from electrodes.

The independent movability of multiple electrode members 26c at each hub 25 can allow for at least one electrode at each hub 25 to extend from the outer member 26b to the patient's scalp (e.g. skin on the patient's head) so that a voltage or current passed through a patient to apply a "shock" to the patient and the patient's bodily response to that "shock" can be sensed by the electrode members 26c and measurement data related to that bodily response can be transmitted to measurement device 7 for use in comparing the first side set of electrode hub data to the second side set of electrode hub data for purposes of assessing whether the patient has experienced a stroke or other neurological injury (e.g. a seizure). The independent movability of the electrode members 26c can also (or alternatively), allow the electrode members at each hub to be positioned for recording the electrical activity of the patient's brain (e.g. sensing and collection of brain electrical activity data for use in Electroencephalography (EEG), etc.). Such collection of data by the electrode members 26c of such data can occur in a passive sense and the use of the data may not necessarily be utilized as part of evaluating the patient's response to an evoked potential.

The independent movability of multiple electrode members 26b at each hub 25 helps ensure that at least one electrode member 26c at each hub 25 can be able to come into contact with a patient's scalp for making suitable contact with the patient's head for sensing the relevant bodily response and providing measurement data to the outer member 26b for transmission to the measurement device 7 and/or another device (e.g. a remote device that may be wirelessly communicatively connected to the hub 25, a device that may have a wired transmission connection to the hub 25, etc.). Upon detection of such a condition, paramedic personnel may route a patient to a stroke specialized hospital or seizure specialized hospital and/or can advise other medical staff at a care facility of the detected condition so that appropriate care can be rapidly provided to the patient upon the patient's arrival at the care facility.

The electrode members 26c can be configured to be coupled to a mechanical biasing mechanism (e.g. a type of spring member, a type of elastomeric spring member, a coil spring powered device, etc.) within the housing 26a that functions to mechanically bias the electrode members 26c to their initial position. The mechanical biasing force provided by the mechanical biasing mechanism can be sufficient to cause the electrode member 26c to move outwardly to its initial position until a patient's head is contacting the electrode member 26c. Contact with the patient's head and the force exerted by the headgear 3 for ensuring a tight fit (e.g. elastic feature of the headgear, strap(s) tightening the headgear onto the patient's head, etc.) can provide the force needed to overcome the mechanical biasing force and permitting the electrode member 26c to move into the chamber 26d and contact the outer member 26b. The mechanical biasing mechanism can include, for example, spring elements within holes, or passageways 26y, of the housing 26a that may contact the electrode members 26c as the electrode members 26c slide in and out of the chamber 26d via passageways 26y that are define in the housing 26a of the hub 25 or other portion of the hub 25. In other embodiments, no such biasing mechanism may be present. And the electrode members may slide in and out of the chamber 26d via the passageways 26y due to gravity or the force of a patient's head being forced into contact with the electrode members' distal ends 26g from the patient wearing the headgear 3.

The frame 23 of the headgear 3 can define the shape and look of the headgear 3 or that frame 23 can be covered within a covering 22. The covering 22 can include an outer shell or a fabric or elastomeric covering that at least partially encloses the frame 23. The covering 22 can be attached to the frame 23 to help facilitate the positioning of the headgear and/or to help attach the headgear to the patient's head so that the headgear 3 has a tight interference fit on the patient's head when the headgear 3 is worn on the patient's head. The first and second strips 1 and 2 can be connected to the frame 23 and/or covering 22 to help with the positioning of the headgear on the patient's head so that the first and second sets of electrode hubs 25 are in the appropriate corresponding mirrored locations on the opposite sides of the patient's head when the headgear 3 is worn by the patient.

Figure 11:
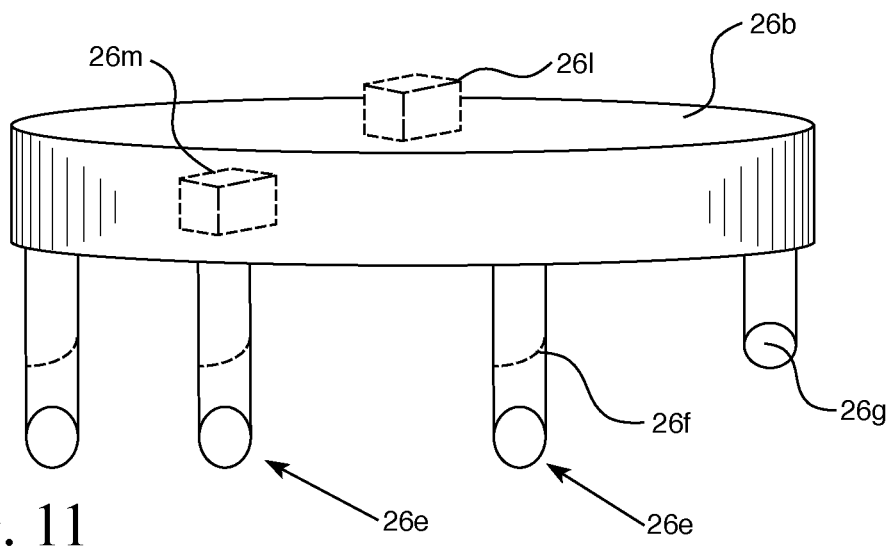
FIG. 11 is a schematic view of another exemplary electrode hub of an electrode array that can be used in embodiments of the headgear.

In other embodiments, the electrode hubs 25 can have a different type of electrode member 26c. For example, as shown in FIG. 11, the electrode hub 25 can include an outer member 26b that is connected to a plurality of telescopable electrode members 26c that can retract from a fully extended position to a retracted position while being connected to the outer member 26b. Each telescopable electrode member can be mechanically biased to its extended position via a mechanical biasing mechanism (e.g. a spring device, etc.). The retraction and extension of the electrode members 26c can occur over a linear path of travel from a retracted position to an extended position and vice versa. The retraction and extension of the electrode members 26c can also occur in a non-linear path or a path of motion that includes linear segments of motion and non-linear segments of motion. For example, the electrode members may spread out along a path of motion that is at an angle or a curved motion as they extend to the extended position and may retract away from such a spread position along an opposite path of motion when retracting. Each electrode member 26c can be structured so that the proximal end is affixed to the outer member 26b while the distal end is moveable via a telescoping connection 26f to the proximal end portion affixed to the outer member 26b (e.g. via welding, molding, adhesive, an interlocking profile, a fastening mechanism, combinations of the same, etc.). Such a configuration can permit some electrode members 26c to stay fully extended for contacting a scalp of a patient's head through the patient's hair while other electrode members 26c may retract due to contact with an object in the patient's hair or a thick strand of hair that impedes the movement of the electrode member 26c sufficiently to overcome a biasing mechanism within the electrode member that biases the electrode member to its fully extended position. The retraction of some electrode members 26c that may be blocked from contact with a patient's scalp can permit other electrode members of the electrode hub 25 to continue to move toward a scalp 30 for contact with a patient's skin without being effected by the blocked electrode members 26c of the electrode hub 25. The independent movement of different electrode members 26c of the electrode hub 25 that is responsive to pressure from a patient related object can allow the headgear 3 to be properly positioned in a relatively tight fit on a patient's head without a blocked electrode member from preventing such positioning and can also allow the electrode hub 25 to have unblocked electrode members 26c properly positioned in contact with a scalp of the patient's head to help ensure the electrode hub 25 can obtain measurement data from the patient at the electrode hub's pre-selected position in the array of electrodes.

Figure 9:
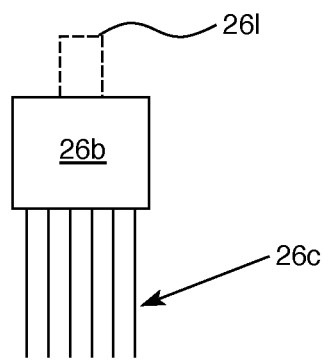
FIG. 9 is a schematic view of an exemplary electrode hub of the electrode array that can be used in embodiments of the headgear.
Figure 10:
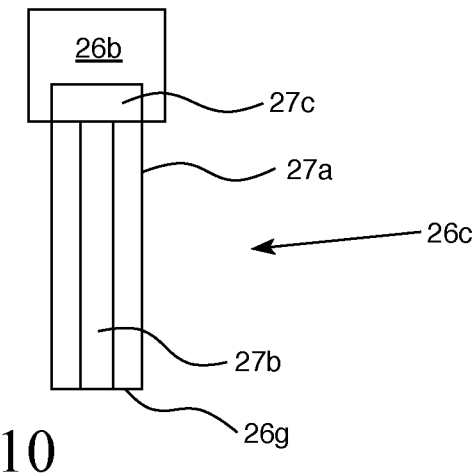
FIG. 10 is a fragmentary view of an electrode member 26c of the exemplary electrode hub of the electrode array shown in FIG. 9.

Referring to FIGS. 9-10, another alternative electrode hub 25 configuration that can be utilized in different electrode hubs 25 of a headgear 3 can include a plurality of electrode members 26c that are attached to outer member 26b and extend from the outer member 26b for contacting a patient's scalp such that the electrode members 26c are flexible. Each of the electrode members 26c can have a root portion 27c attached to the outer member 26b and an inner body made of a flexible material (e.g. a polymeric material, a flexible metallic material, etc.) that extends from the root portion 27c and extends out of and away from the outer member 26b. For embodiments that have an inner body 27b composed of a polymeric or elastomeric material or other type of non-conductive material, the inner body 27b can be coated in an outer covering that is comprised of an electrically conductive material (e.g. copper, aluminum, gold, silver, etc.). The outer covering 27a may be a relatively thin layer of electrically conductive material that can fully enclose at least the portion of the inner body 27b that extends from the outer member 26b to provide an electrically conductive coupling from the electrode member 26c to the outer member 26b for the transmission of measurement data. The inner body 27b can be sufficiently thick relative to the outer covering 27a so that the flexibility of the inner body 27b can permit the electrode member to flexibly move around any hair or other element that may be present on a patient's head that could pose a blockage element that could prevent the electrode member's distal end from contacting the scalp of the patient. The outer covering 27a can be configured as a film, an enclosing layer, coating, or other type of covering. The flexible motion of the electrode member 26c can allow the electrode member to bend or flex around objects or to compress in response to a blocking element such that at least some of the electrode members 26c are able to have their distal ends 26g contact the patient's scalp when the headgear 3 is worn by a patient in the desired location on the patient's head.

In yet other embodiments, the electrode members 26c can be composed of an electrically conductive material (e.g. gold, silver, copper, aluminum, etc.) and can be structured to be flexible without requiring use of an outer covering 27a. Such flexibility can be configured due to the length, width, and thickness of the electrode member. For such embodiments, the proximate end of each electrode member can be attached to an outer member 26b at a root portion 27c and have an opposite distal end that is for contacting the scalp of a patient's head.

In yet other embodiments, such as the embodiment shown in FIGS. 14-20, the distal end 26g of each electrode member can include a plurality of flexible members 26z that are configured to bend or flex around objects or to compress in response to a blocking element such that at least some of the electrode members 26c are able to have their distal ends 26g contact the patient's scalp 30 when the headgear 3 is worn by a patient in the desired location on the patient's head.

In other embodiments, such as the embodiments shown in FIGS. 14-20 and 6-8, the proximal end 26h of each electrode member 26c can be moveable from a first position in which the proximate end is spaced apart from the outer member 26b and a second position in which the proximal end 26h is in contact with the outer member 26b. The proximal end 26h can be moveable to any of a number of different third intermediate positions between the first and second positions as well. The path of motion of the electrode members can be defined by a part of a housing 26a that defines a chamber 26d in which the proximal ends 26h are moveable. For instance, a portion of the housing 26a can define passageways 26y. Each passageway 26y can define a path of motion about which the electrode member pensionable within that passageway is moveable into and out of the chamber 26d and/or between the first and second positions of the electrode member 26c. The path of motion for the electrode member can be defined so that the electrode members move linearly between their first and second positions or move in a non-linear fashion (e.g. passageway 26y can be defined to be a straight passageway through which a portion of the electrode member 26c is passable or can be structured to define a curved passageway through which a portion of the electrode member 26c is passable, etc.). The outer member 26b having at least one transmission circuit 26e can be incorporated into the housing 26a to help define a part of this chamber 26d so that the proximal ends 26h can be moved into contact with the outer member 26b or can be moved into contact with an element of the hub housing 26a that defines the chamber 26d that is conductively connected to the outer member 26b so that, upon contact of the proximal ends with that element, the electrode member 26c is conductively connected to the outer member 26b and the at least one circuit 26e of the outer member 26b.

In some embodiments, it is contemplated that a proximal end 26h of each electrode member can include a stop body 26i that can be positionable within the chamber 26d and be configured to receive proximal end 26h of the electrode member 26c when the member moves from its first initial position to its second position. The stop body 26i can be composed of a conductive material. The stop body 26i can be sized so that it cannot pass through the passageway 26y through which a portion of the electrode member is passable. The stop body 26i can be configured as a root portion to help keep that root portion within the chamber 26d. In some embodiments, it is contemplated that the stop body 26i can moveably receive a portion of the electrode member 26c within a groove or cavity such that the a portion of the electrode member 26c can move within the stop body 26i as the electrode member passes through the passageway 26y when moving between its first and second positions. In other embodiments, a portion of the electrode member 26c may be affixed in a non-moving attachment to the stop body 26i of the proximal end 26h of the electrode member 26c.

Referring to FIGS. 21-26, each electrode hub 25 can include a housing 26a that includes a compressible portion that defines a collapsible cavity 33 therein. The cavity 33 can retain a conductive fluid material EF (e.g. a gel, a liquid, a slurry, etc.). The conductive fluid material EF can be comprised of at least one electrolyte. The electrolyte can include, for example, salt (e.g. NaCl) or other type of conductive material (e.g. flakes of a conductive metal (e.g. silver, gold, or copper, etc.), solid particulates of a conductive material such as copper, gold, or aluminum, etc.) within a liquid (e.g. liquid water) or a gel composition (e.g. aloe vera gel, a silicone gel, etc.) having a composition that provides for electrical conductivity. Example gels can include a thickened aqueous mixture and a salt or polarizing substance that are present in a sufficient concentration to facilitate the making of electrical contact with the skin of a patient to help improve the electrode member conductive connection with the skin to try and limit areas of poor or intermittent contact, which, when present, can result in the generation of spurious electrical signals. Example of such a gel are disclosed in U.S. Pat. Nos. 4,406,827 and 5,348,686.

The cavity 33 can be a chamber 35 that is defined by a top portion or upper portion of the housing of the hub 25 that is in communication with electrode members 26c so that the conductive fluid material stored in or retained in the cavity 33 can be passed out of the cavity 33, through the electrode members 26c, and emitted out of discharge holes 37 of the electrode members 26c. The one or more discharge holes 37 for each electrode member 26c can be positioned on at least one side of the electrode member 26c.

In some embodiments, each electrode member 26c can have only a single discharge hole 37. In other embodiments, there may be multiple different discharge holes 37 positioned along a length of the outer surface of the electrode member 26c. The discharge holes 37 can be in fluid communication with channels 39 defined inside the electrode member 26 that are positioned around a conductor 32 of the electrode member 26c. The channels 39 can be defined by splines, fluid conduit members positioned in the body of the electrode member 26c, insert members, portions of the electrode member 26c, or other fluid conduit defining element positioned inside the electrode member 26c that is in fluid communication with the cavity 33. The outermost surface of the electrode member 26c that encloses the conductor 32 so that one or more channels 39 are defined between the outermost surface and the conductor 32 can include a film or conductive coating on a hollow outer structure) in some embodiments (e.g. a polymeric tubular structure having such a coating on its outer surface, etc.)

In some embodiments, the channels 39 can be defined by hollow spines or other fluid conduit defining element positioned in the electrode member 26c between the outermost surface of the electrode member and the conductor 32. The hollow spines can be in fluid communication with the cavity 33 and the discharge holes 37 so that fluid is passable from the cavity 33 and out of the discharge holes 37 via the channels 39 defined by the splines. In other embodiments, each electrode member 26c can have a single annular channel (indicated by broken line as single annular channel 39a in FIGS. 23 and 24) defined between the conductor 32 and the outer surface of the electrode member 26c that is in fluid communication with one or more discharge holes 37 and the cavity 33.

The channels 39 and discharge holes 37 can be designed and configured so that the conductive fluid material EF that can be output from the cavity 33 is directed out of the discharge holes 37 at a desired flow rate and direction so that the conductive fluid material EF flows along a pre-selected flow path 41 to a pre-selected target area 43 on a scalp 30 of a patient or on a surface that the conductor members 26c can be contacting or engaging. The flow path 41 can be configured to define a centralization flow path 41a to direct the conductive fluid material toward a central target area 43 that may be aligned with a center of the electrode hub 25 between the electrode members 26c extending from that hub. In other embodiments, the flow path 41 can be configured to define a non-centralized flow path 41b to direct the flow rate and direction of the conductive fluid material to a non-centralized target area 43. Some electrode arrays of headgear 3 can be configured to utilize a centralized target area 43 via a centralization flow path 41a while others may be configured to direct the conductive fluid material to an off-center target area 43 via a non-centralized flow path 41b. Other embodiments can be configured so that all the electrode hubs 25 utilize the same type of flow path configuration.

The flowing of the conductive fluid material EF along a flow path 41 to a target area 43 can cause the conductive fluid material to be positioned on the scalp of a patient or other skin surface of the patient along the entirety of the flow path 41. For example, as the conductive fluid material flows to the target area, a portion of the conductive fluid material may be left behind to reside on the skin surface that is along the flow path due to friction and/or other property of the conductive fluid material (e.g. viscosity, etc.). The use of the flow paths and the directing of the flow paths toward a target area 43 can permit the conductive fluid material to be distributed throughout an entire region between the discharge holes and the target area 43. The conductive fluid material EF can also spread out as it moves along the flow path to the target area 43 (e.g. some of the conductive fluid material can move laterally as the conductive fluid material moves in a flow direction toward the target area 43 such that the conductive fluid material spreads out as it moves in a flow direction along the flow path as indicated by spreading out indicators 44 in FIGS. 25-26). Such a spreading out can occur from a thickness of the conductive fluid material that may be emitted from the discharge holes 37 changing as the conductive fluid material moves along a scalp due to gravity's effect on the conductive fluid material, the viscosity of the conductive fluid material, and the flow rate of the conductive fluid material moving along the patient's skin. The spreading out can occur in a direction that is transverse to and/or perpendicular to the direction at which the conductive fluid material flows toward the target area 43.

While the conductive fluid material EF may be moved in the flow direction dictated by the discharge hole 37, the spreading out can also be defined by the dimensions of the discharge holes to help define a desired conductive fluid material deposition occurring as the conductive fluid material moves along the flow paths 41 to the target area 43. For example, material discharged out of smaller sized discharge holes 37 can have a smaller stream size and spread out less as the material moves along its flow path 41 as compared to conductive fluid material emitted out of larger sized discharge holes 37. Further, the flow rate of the conductive fluid material discharged out of the larger discharger holes may be slower than the flow rate of material discharged out of smaller holes (in which the same force is applied for driving the conductive fluid material out of cavity 33 for emission out of the discharge holes 37). The size and dimensions of the channels 39 and discharge holes 37 can be configured to provide a desired flow path 41 as well as a pre-selected material spread out pattern to provide a pre-selected conductive fluid material deposition area via flowing of the conductive fluid material along the flow paths 41 to the target area 43.

The flow rate of the conductive fluid material EF can be set based on how the cavity 33 is compressed from an uncompressed state to a compressed state in addition to the size and configuration of the channels 39 and the discharge holes 37. In some embodiments, the regulation or actuation of such a compression can be achieved manually by a user pressing on the collapsible housing 26a of each hub 25 to collapse the cavity 33 at different times to push the conductive fluid material out of the cavity 33 and through the channels 39 so it is emitted out of discharge holes 37 along a flow path 41. Alternatively, each electrode hub 25 can include a mechanical collapsing actuator that can be configured to contact the housing 26a of the hub body 26 and engage the housing 26a to collapse the cavity 33 within the housing 26a for pushing the conductive fluid material out of the cavity and out of the discharge holes 37 via the channels 39. Such a mechanical collapsing actuator can be a piston mechanism, a gas spring, a pressing lever, or other type of actuation mechanism that may contact conductive fluid material in the cavity 33 to drive motion of the material out of the cavity 33. In some embodiments, the cavity 33 may not collapse when the conductive fluid material is driven out of the cavity. Instead, a piston member or other flow directing member may move within the cavity 33 to effectively shrink the size of the cavity to push conductive fluid material out of the cavity.

The housing 26a defining the cavity 33 or chamber within the housing 26a defining the cavity 33 can be composed of a flexible or resilient material so that the housing 26a and electrode members 26c can be used repeatedly. For example, the housing 26a can be configured to move into a collapsed state and subsequently resiliently return to the uncollapsed, expanded state, after the force used to collapse the cavity 33 is removed. More conductive fluid material can then be inserted into the cavity for the electrode hub to be reused (e.g. a removable cap 34 can be provided on the housing to permit the cavity 33 to be accessed for refilling the conductive fluid material into the cavity via a threaded connection between the cap and the housing 26a or other type of releasable attachment mechanism).

Alternatively, the cavity 33 can be collapsible into one or more intermediate collapsed states before being moved to a fully collapsed state. Initial collapsing of the cavity 33 can be utilized for a first measurement. The cavity 33 can then be further collapsed to apply further conductive fluid material out of the discharge holes 37 for repeated uses until the cavity 33 is fully collapsed. Once fully collapsed, the housing 26a can be structured so that the electrode hub must be replaced with a new hub or so that the cavity is resiliently moveable back to an initial uncompressed position by removing of the compressing force used to collapse the cavity 33 so that the cavity can be re-filled with conductive fluid material for further uses of the electrode hub 25.

Embodiments of the electrode hub 25 utilizing the discharge holes 37 for emitting conductive fluid material for flowing that fluid toward a target area 43 and having that material spread out as it flows toward that target area can also permit the electrode member 26c to be impregnated with the conductive fluid material so that the conductive fluid material contacts patient skin and conductor 32 of the electrode member 26c for providing an improved electrically conductive connection between the patient's skin and the electrode member 26c. For example, when the conductive fluid material is passed from the cavity 33 and out of the discharge holes 37, a remainder impregnation portion of the conductive fluid material 33 can be retained in the one or more channels that surround the conductor 32 and also be present at a distal edge 26g of the electrode member 26c that is to be positioned for contacting or engaging the patient's head for an electrically conductive connection to the patient's skin. The portion of the conductive fluid material EF that is at the distal edge 26g of the electrode member 26c can be passed there via a discharge hole at the distal edge 26g or by some of the conductive fluid material passing out of a discharge hole on a side of the electrode member and moving along the outer surface of the electrode member 26c to the distal edge. The conductive fluid material can be configured to help provide an environment on the patient's skin adjacent the electrode member 26c that provides an ionic conductive path to allow for the capture of the patient's bioelectric signals via the electrode member 26c.

The use of the conductive fluid material being passed through the electrode member 26c can permit the electrode members 26c of the electrode hub 25 to function as a wet or semi-wet electrode in which the conductive fluid material is applied at the site of contact or engagement between the electrode members 26c and the patient's skin instead of having to be applied prior to placement of the electrodes on a patient via a separate applicator mechanism (e.g. a tube of gel or liquid being squeezed to apply the material on a site at which an electrode is to subsequently be placed, etc.).

In some alternative embodiments, the cavity 33 that is collapsible for delivering conductive fluid material out of one or more discharge holes 37 can be collapsible without an external housing 26a of the electrode hub 25 being compressed. For instance, there may be an internal piston mechanism within the housing 26a that can be actuated for motion to drive conductive fluid material out of the cavity 33 via pressing a button on the external surface of the housing 26a that is attached to a piston mechanism to facilitate movement of a piston member to drive a flow of the conductive fluid material out of a cavity 33 inside the housing 26a through the channels 39 and out of at least one discharge hole 27. A spring or other type of biasing mechanism can be connected between the piston member and the button to bias the button to an initial position (e.g. a non-depressed position). Such embodiments can be configured to facilitate refilling a cavity 33 with material when the button is in a non-depressed position for embodiments that are designed for repeated uses.

In yet other embodiments, a piston mechanism can be actuatable via a controller that can receive control signals from a controller device via a wireless communication connection (e.g. Bluetooth or near filed communication connection) or a wired connection. Actuation of the piston mechanism in such embodiments can be effected via a user manipulating a button or other input mechanism of a measurement device 7 for example.

In yet other embodiments, conductive fluid material EF can be provided via use of an injector device P that may be releaseably attached to the headgear 3. The injector device can be, for example, a syringe, an injector pen, or other type of injector that has a reservoir of conductive fluid material EF that is injectable out of the device. The injection of fluid can be actuated by a manual pressing on a plunger or other type of injection actuation mechanism of the injector device P. The injector device P can be configured to be releasably connectable to the headgear 3 via clasp, a resiliently receiving jaw that is configured to resiliently hold the injector device P, a receptacle connected to the headgear, or other type of releasable connection mechanism. The injector device P can be configured so that it is reusable for applying conductive fluid material EF multiple times or be configured as a single use device that is to be replaced with a new injector device after the injector device is used to apply conductive fluid material EF onto a patient's head or onto electrode members 26c prior to the headgear being positioned on a patient's head.

The injector device P can be configured so that the injector device can be pulled off of the headgear and actuated so that conductive fluid material EF is positioned on sites on the scalp 30 at which the electrode hubs are to be positioned. Alternatively (or in addition), the conductive fluid material EF can also be injected onto the distal ends or other portion of electrode members 26c prior to the headgear being positioned on a patient. The application of the conductive fluid material EF may occur prior to any testing of a patient is performed. Alternatively (or in addition), the use of the injector device P to apply the conductive fluid material EF may occur in response to an identification of a poor quality or unacceptable electrically conductive connection at one or more of the electrode hubs (e.g. seeing LED indicator 261 in a red or yellow color as discussed herein, observing electrode indicia 9c in a red or yellow color as discussed herein, etc.). In response to identifying a poor quality connection, the headgear 3 can be removed from a patient and the injector device can be removed from the headgear and used to inject conductive fluid material EF onto the patient and/or on to the electrode hubs (e.g. at least electrode members of the hubs that had the poor quality connections).

Figure 12:
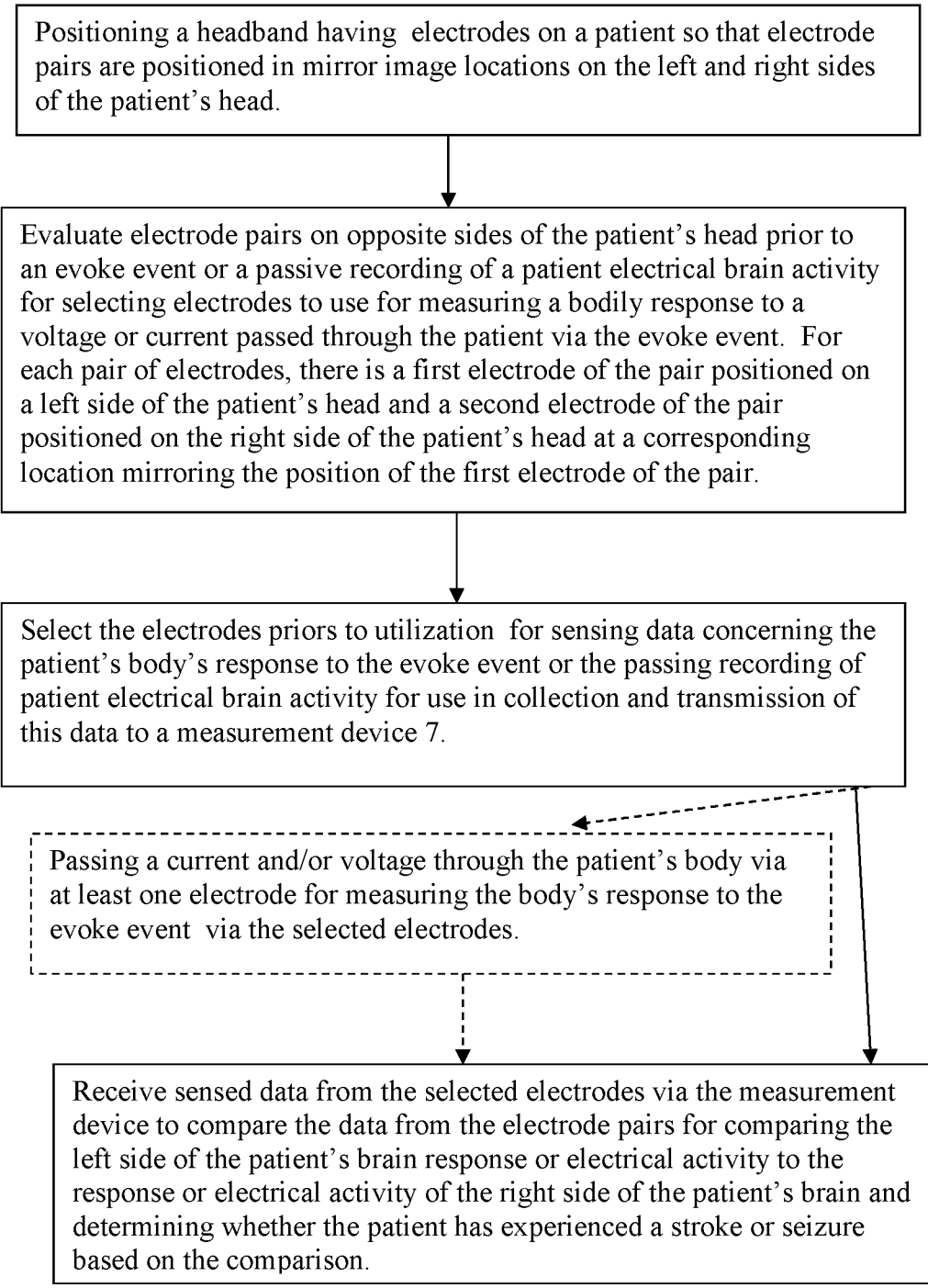
FIG. 12 is a flow chart illustrating a first exemplary embodiment of a method of using an electrode array of a headgear to assess a neurological condition of a patient.
Figure 13:
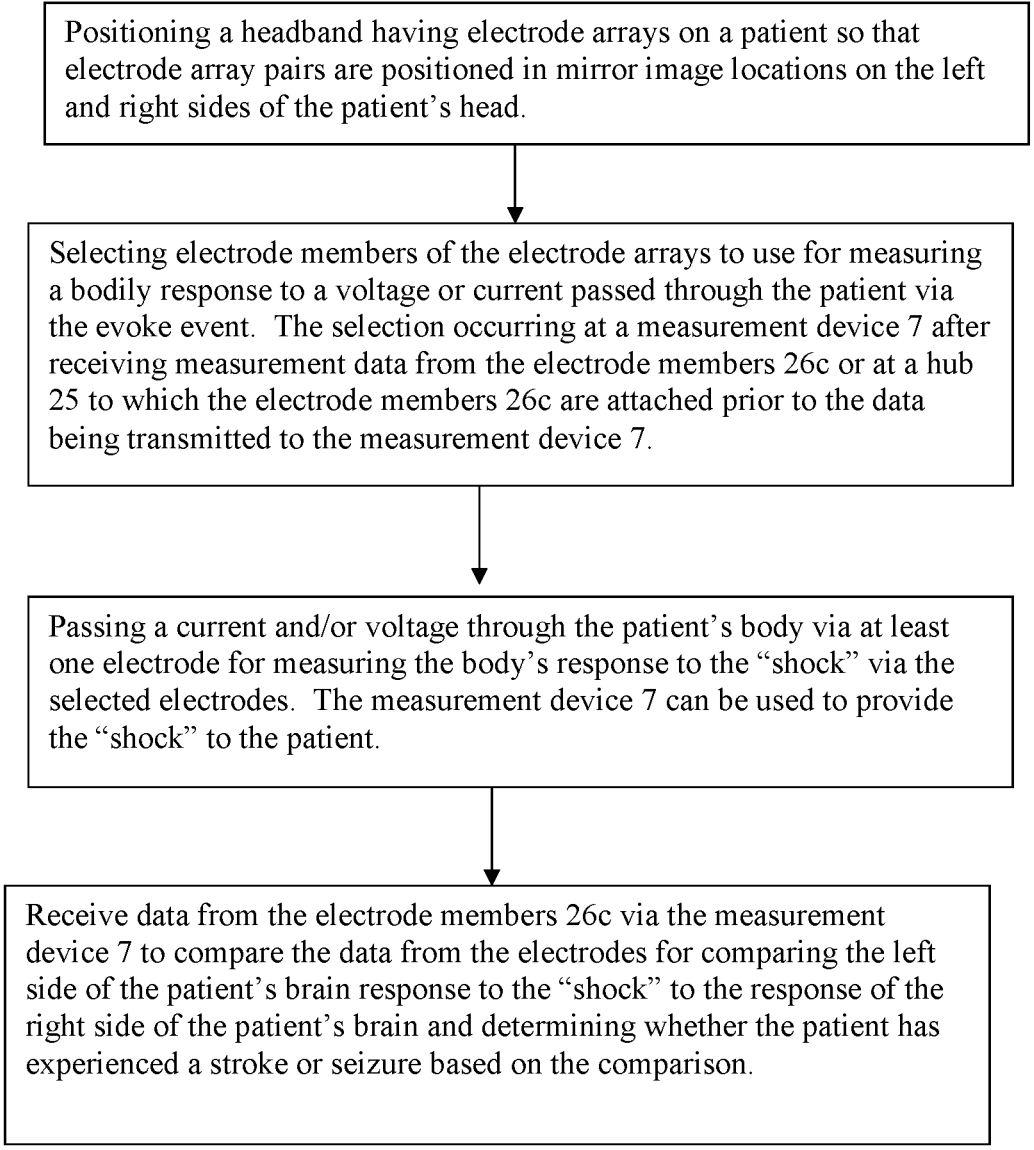
FIG. 13 is a flow chart illustrating a second exemplary embodiment of a method of using an electrode array of a headgear to assess a neurological condition of a patient.
Figure 14:
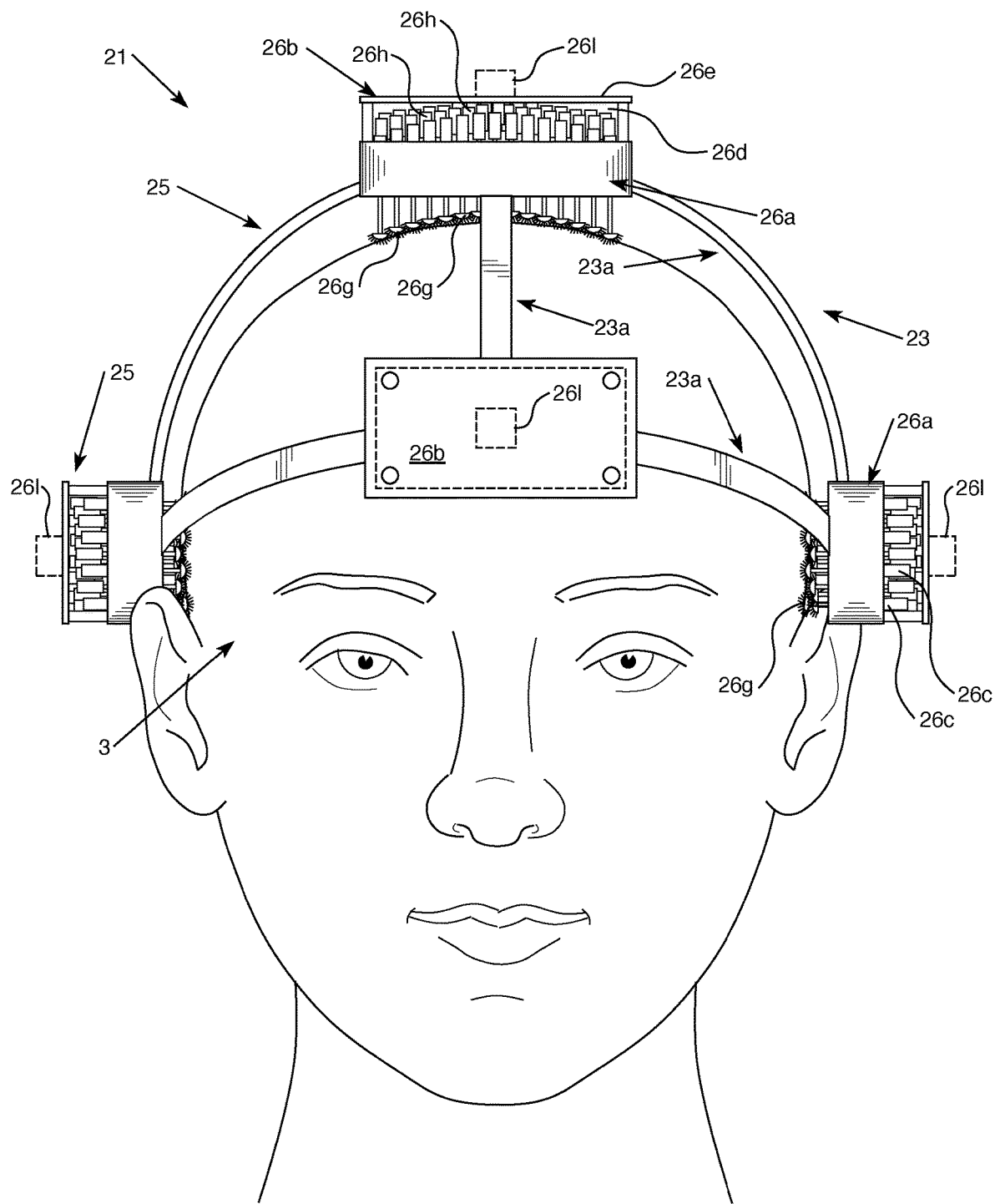
FIG. 14 is a front perspective view of a third exemplary embodiment of the headgear having the electrode array.
Figure 15:
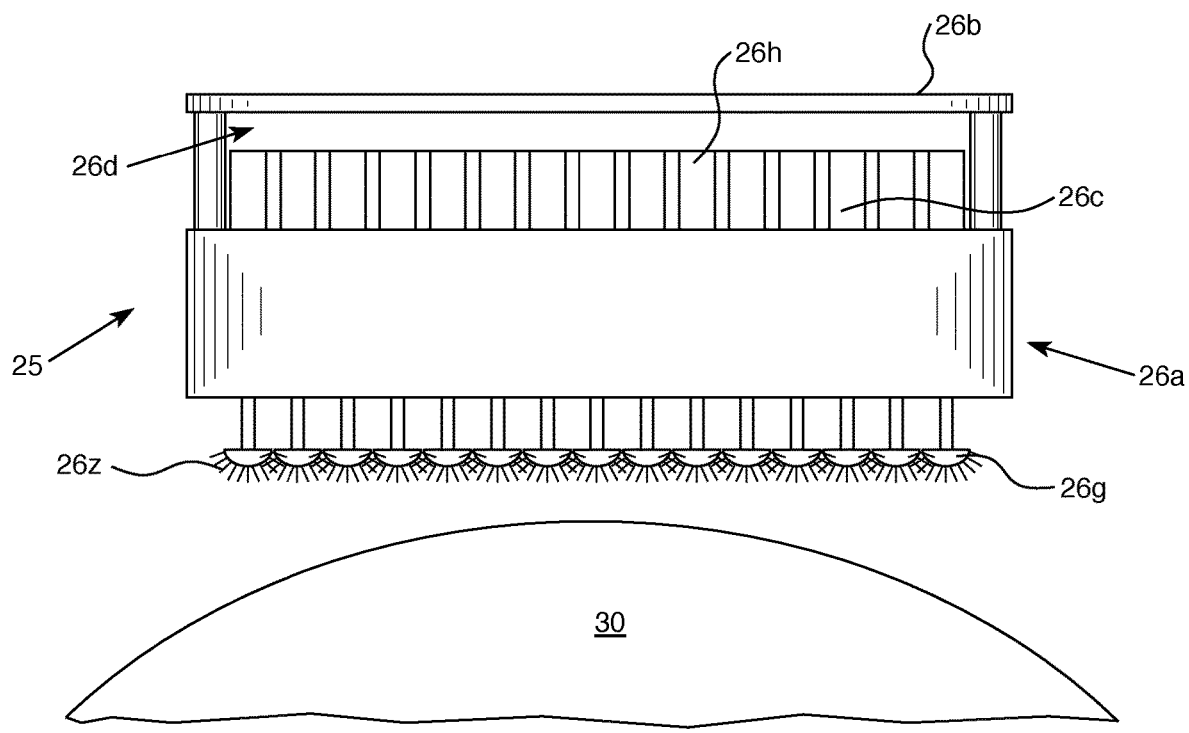
FIG. 15 is an enlarged fragmentary view of an electrode hub of the third exemplary embodiment of the headgear with the electrode members shown in a first position.
Figure 16:
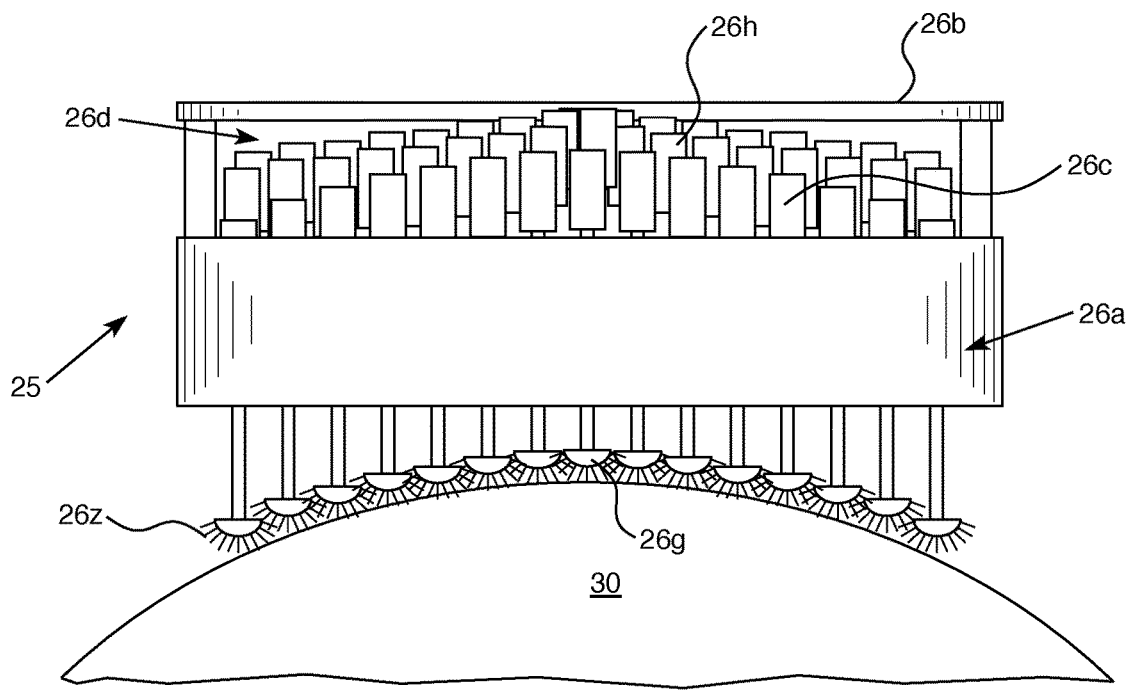
FIG. 16 is an enlarged fragmentary view of an electrode hub of the third exemplary embodiment of the headgear with the electrode members shown in a second position.
Figure 17:
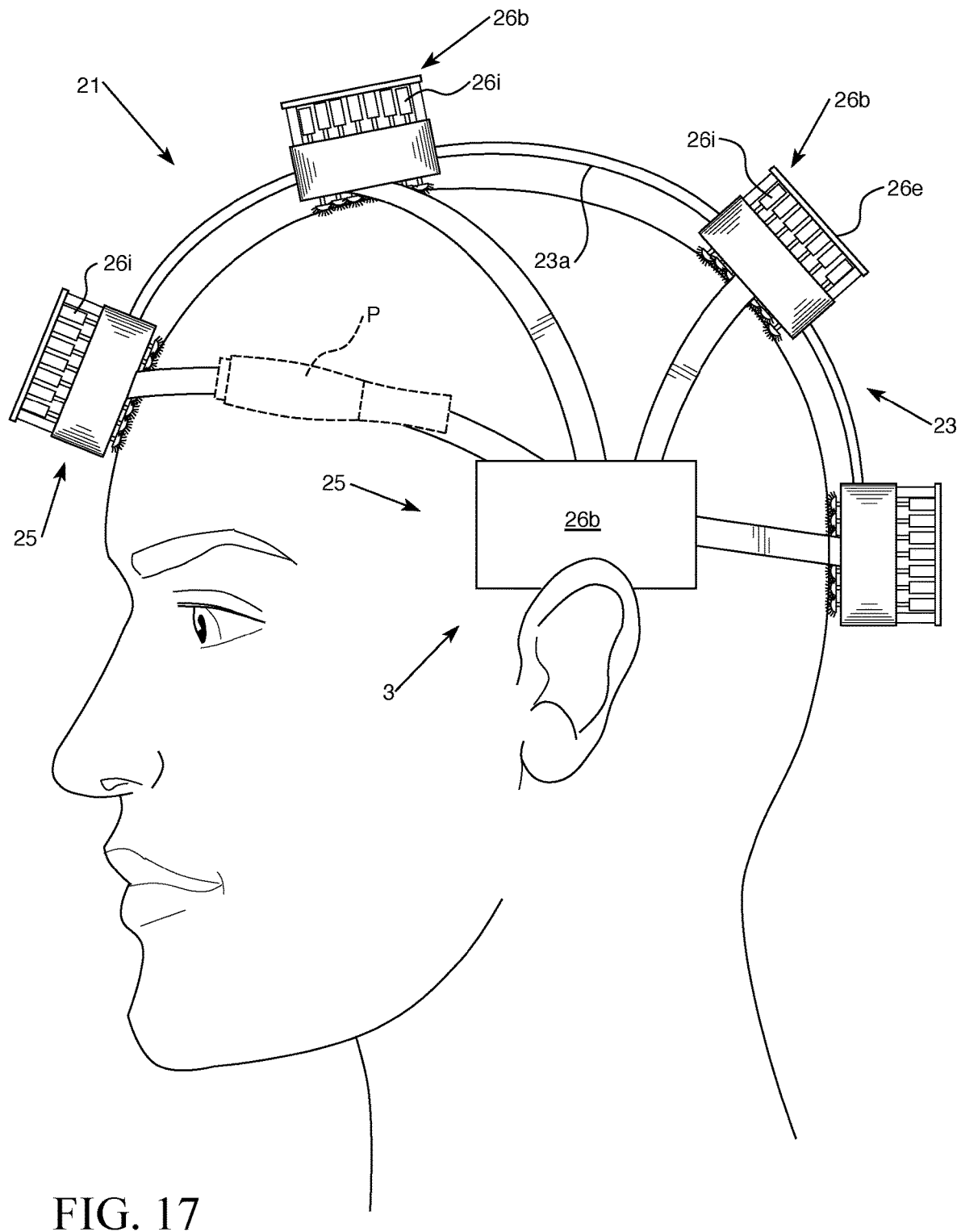
FIG. 17 is a perspective left side view of the third exemplary embodiment of the headgear having an electrode array that is being worn by a patient. The right side view of the embodiment shown in FIG. 17 would be a mirror image of the left side view shown in FIG. 17.
Figure 18:
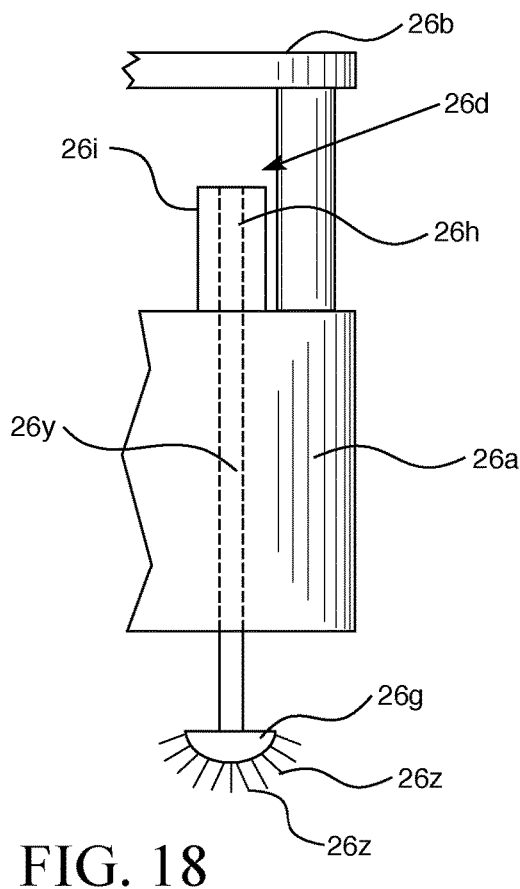
FIG. 18 is a fragmentary view of an electrode member 26c of an exemplary electrode hub of the electrode array of the third exemplary embodiment of the headgear in the first position.
Figure 19:
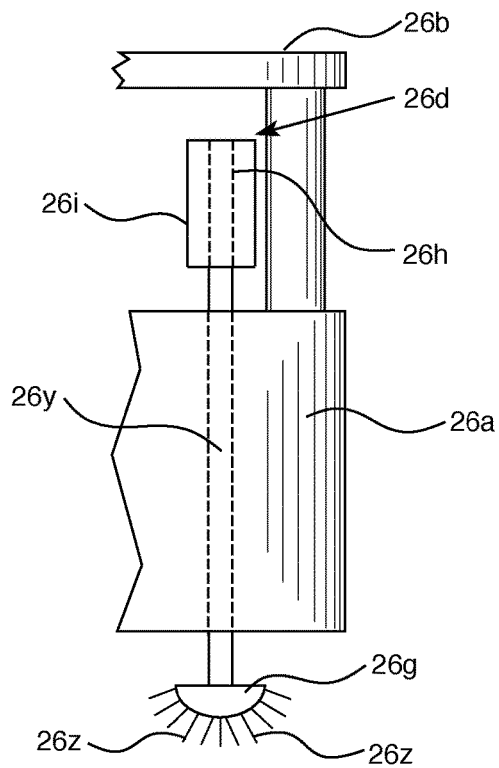
FIG. 19 is a fragmentary view of an electrode member 26c of an exemplary electrode hub of the electrode array of the third exemplary embodiment of the headgear in an intermediate third position that is between the first and second positions of electrode member.
Figure 20:
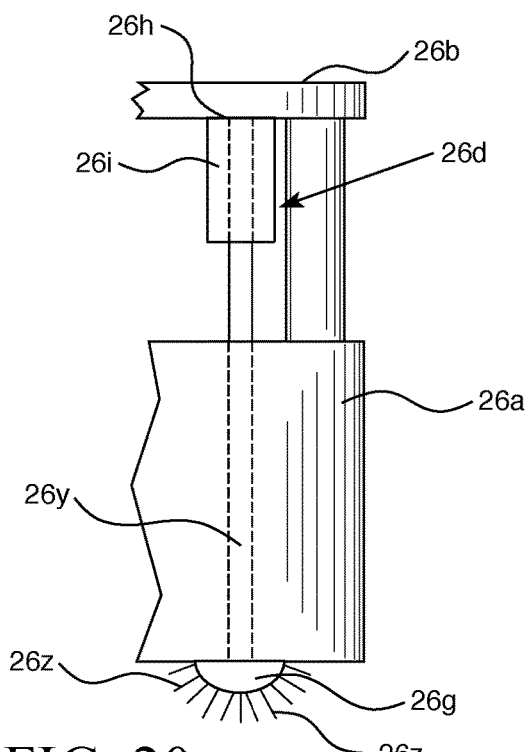
FIG. 20 is a fragmentary view of an electrode member 26c of an exemplary electrode hub of the electrode array of the third exemplary embodiment of the headgear in the second position.
Figure 21:
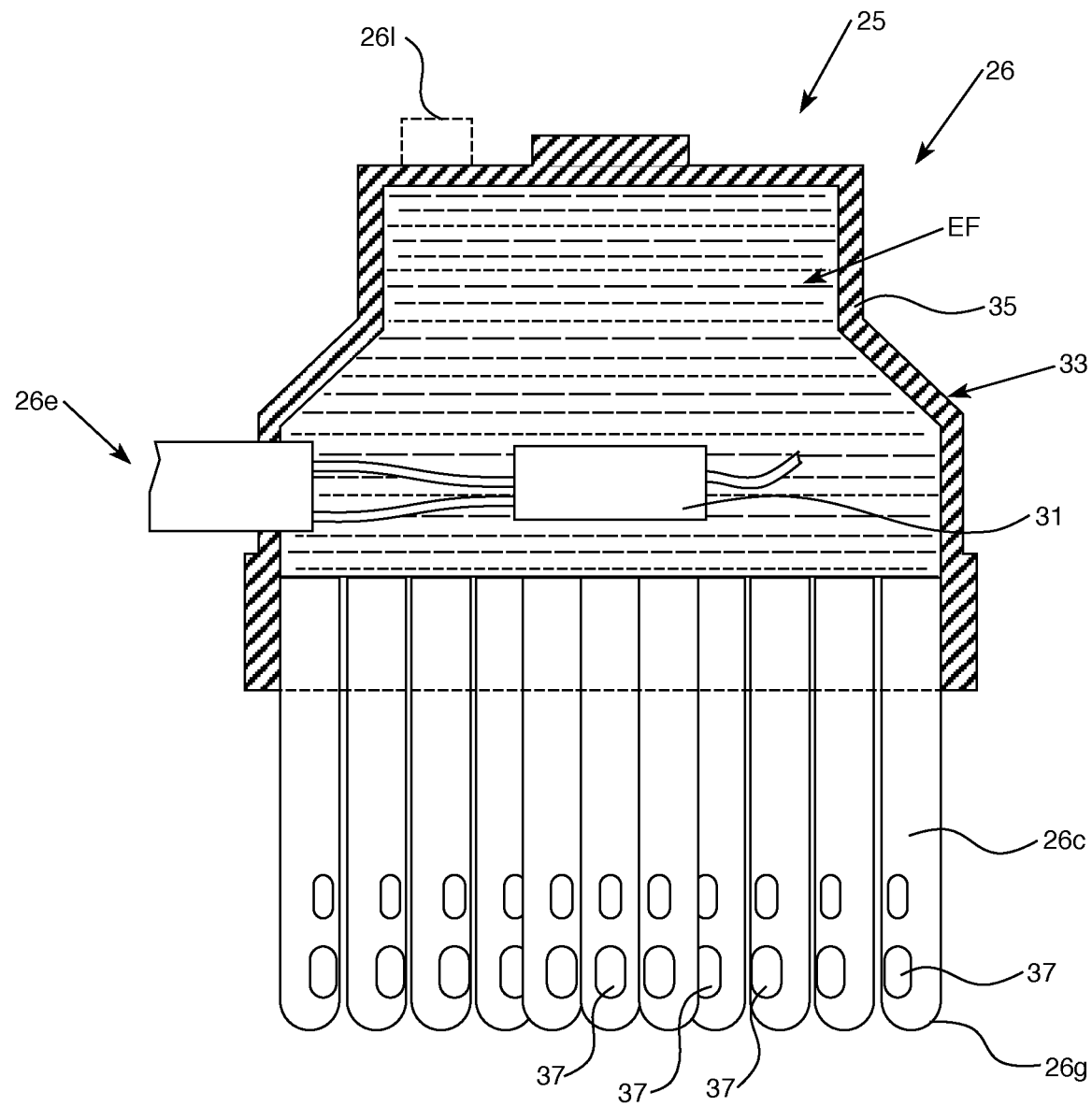
FIG. 21 is a perspective view of an exemplary electrode hub of an electrode array can be included in the first, second, or third embodiments of the headgear or other embodiment of the headgear with the hub having a compressible chamber in a first position (e.g. an uncompressed position or an initial position).
Figure 22:
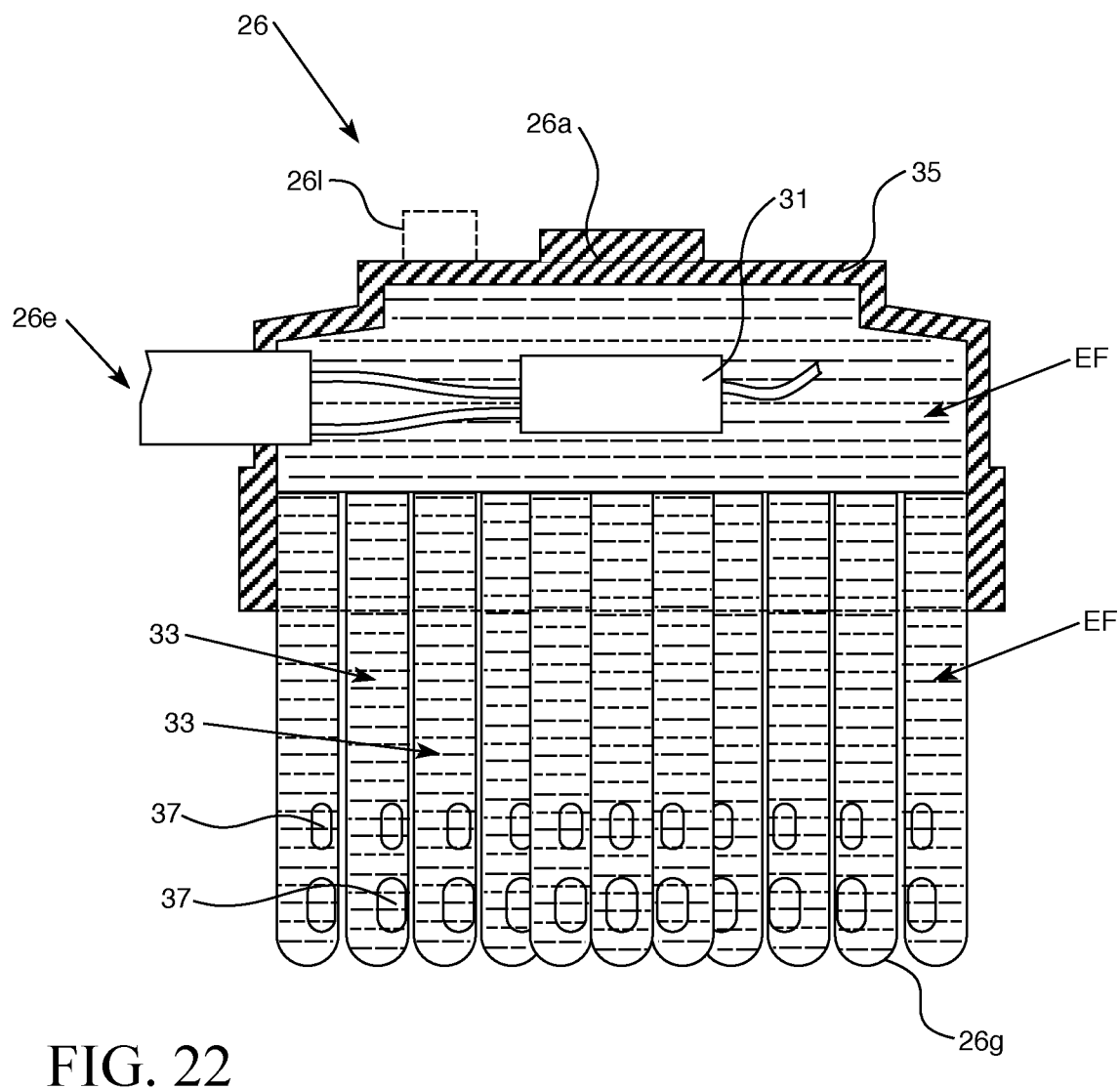
FIG. 22 is a perspective view of the exemplary electrode hub of an electrode array can be included in the first, second, or third embodiments of the headgear or other embodiment of the headgear shown in FIG. 21 with the compressible chamber in a second position (e.g. a compressed position or a collapsed position).
Figure 23:
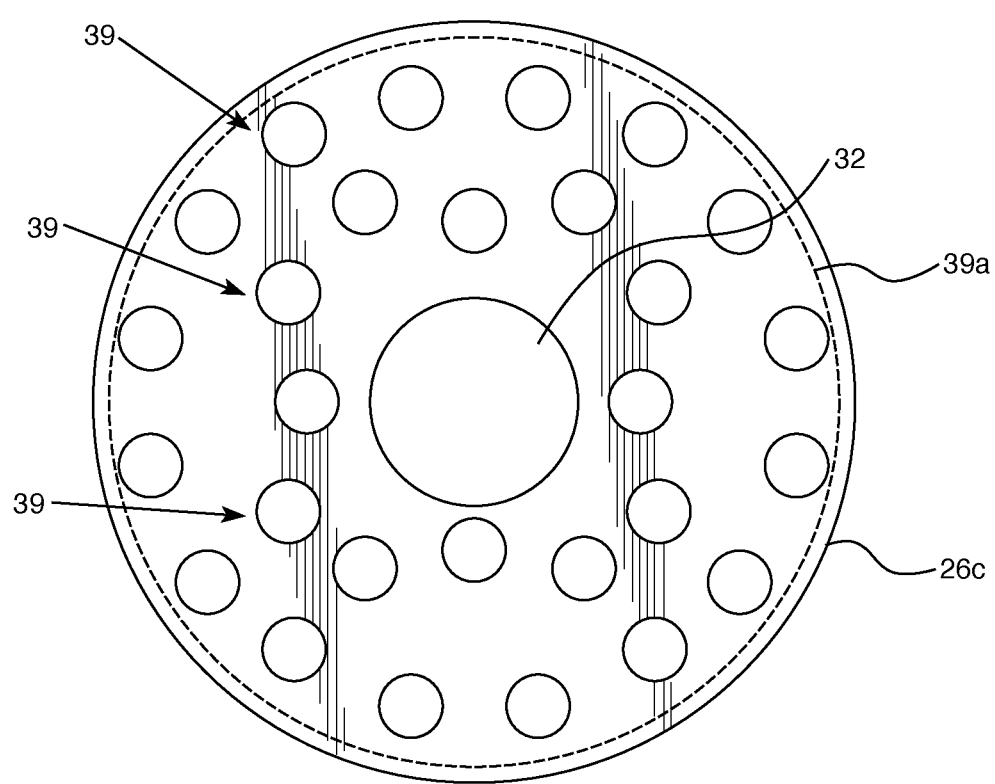
FIG. 23 is a cross-sectional view of an exemplary electrode member of the electrode hub embodiment shown in FIGS. 21 and 22 to illustrate hollow channels through which a conductive fluid material (e.g. a slurry, a gel, etc.) is passable for being directed out of the electrode member and onto skin of a patient.
Figure 24:
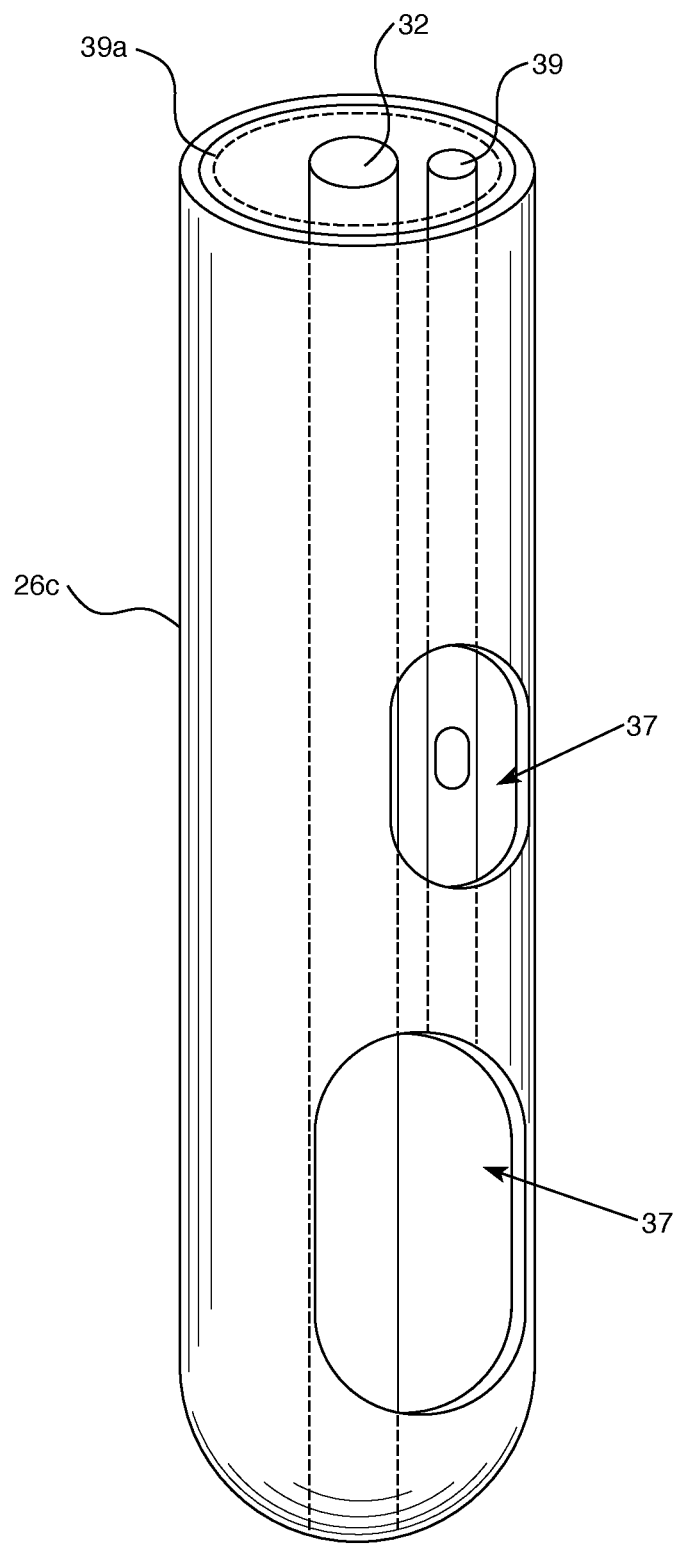
FIG. 24 is a perspective view of an exemplary electrode member of the electrode hub embodiment shown in FIGS. 21 and 22 having multiple channels 39 defined in channel members (e.g. splines, inserts, portions of the electrode member body, etc.) cut away to illustrate discharge outlets for through which conductive fluid material (e.g. a gel, a liquid, etc.) is passable for being directed onto the skin of a patient to improve or facilitate a conductive connection between the electrode and the patient.
Figure 25:
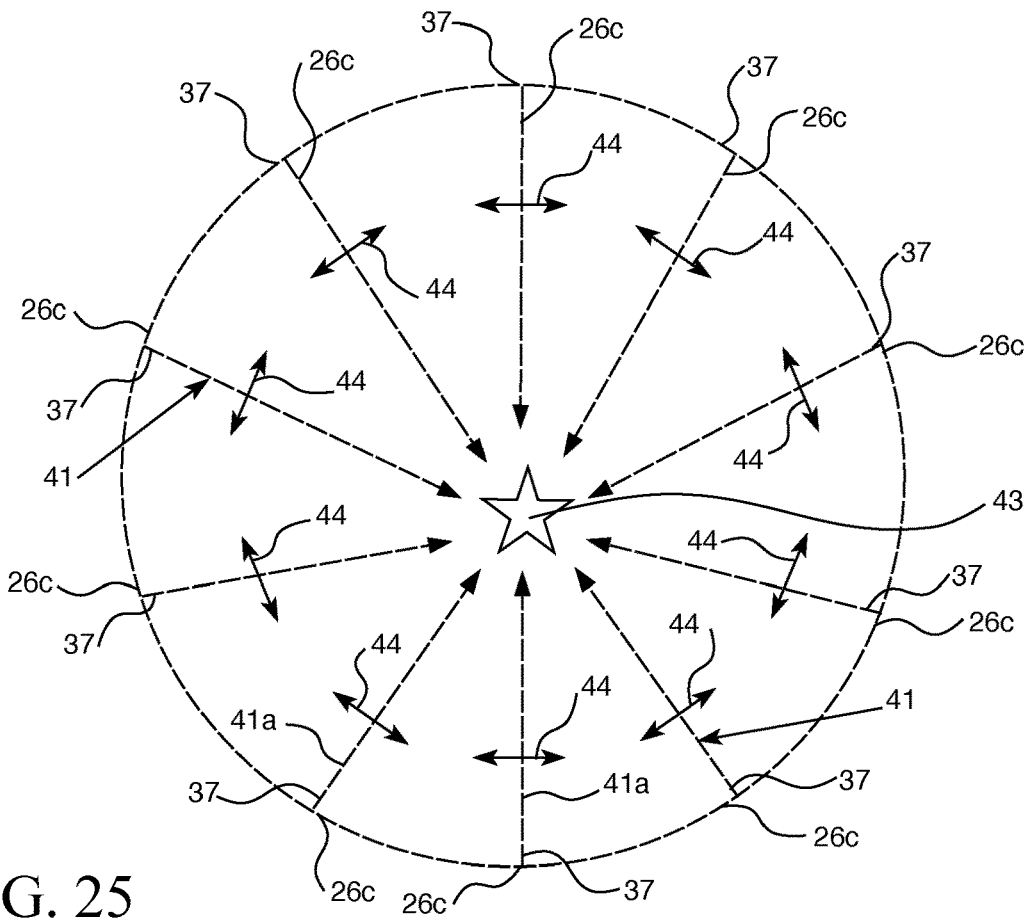
FIG. 25 is a schematic representation of a first preselected fluid flow pattern of fluid emitted from the discharge outlets of the electrode members of the exemplary electrode hub shown in FIGS. 21-22 based on the flow rate of fluid emitted from the electrode members and the placement and orientation of the discharge outlets of the electrode members to provide a flow of fluid directed to a pre-specified target area.
Figure 26:
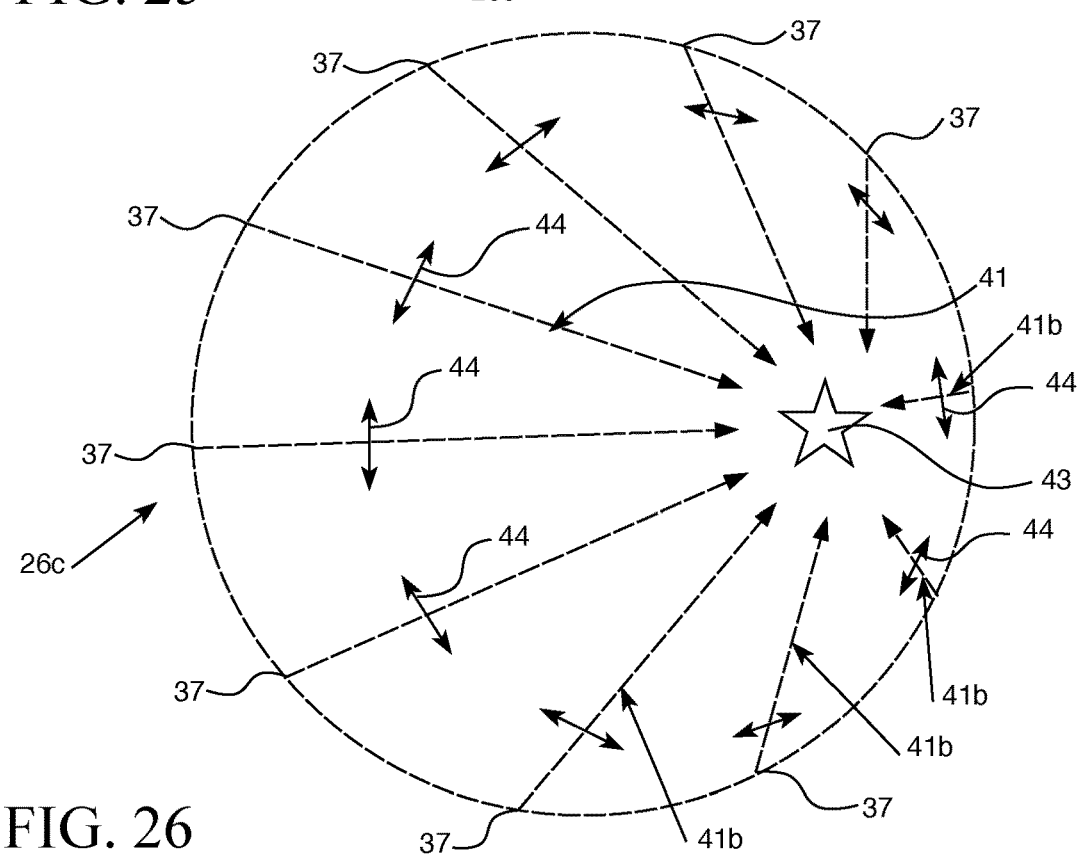
FIG. 26 is a schematic representation of a second preselected fluid flow pattern of fluid emitted from the discharge outlets of the electrode members of the exemplary electrode hub shown in FIGS. 21-22 based on the flow rate of fluid emitted from the electrode members and the placement and orientation of the discharge outlets of the electrode members to provide a flow of fluid directed to a pre-specified target area.

Referring to FIGS. 12 and 13, testing or evaluation of a patient via measurement device 7 and headgear 3 with electrode arrays 25 can be provided in which certain electrode members 26c are used in a particular measurement for a patient. In such methods, a selection can be made in a passive or active configuration so that only certain electrode members 26c, or certain electrode hubs 25 are utilized for a particular evaluation or measurement. In some embodiments, certain hubs may be selected. In other embodiments, all the hubs 25 may be utilized, but certain electrode members 26c of the hubs 25 may not be utilized while other electrode members 26c at each hub 25 are used. The determination of which electrode members 26c are to be used (or which measurement data from which electrode members 26c or hubs 25 is to be used) in a measurement or an evaluation can be determined at the hub 25 or at the measurement device 7. The selection of which electrode members 26c are to be used can occur prior to the providing of an evoke event by a patient being administered a "shock" (e.g. a current or voltage) to evoke a response to that "shock". The selection can alternatively occur at the time the "shock" is administered to the patient or after measurement data is received from electrode members 26c concerning the patient's response to the "shock" at the outer member 26b or at the measurement device 7.

The selection of electrode members 26c or hubs 25 can also (or alternatively) occur prior to, during, or after, the electrode members 26c or hubs 25 being utilized for collecting electrical activity data of a patient's brain that can be utilized for EEG. The use of the electrode members 26c or hub for EEG purposes can occur without any need or desire to evaluate a patient's response to an evoked potential and/or can occur in connection with such a diagnostic procedure.

In some embodiments, some electrode members 26c may not be positioned in contact with the scalp of a patient's head due to hair or other blockage element. Such electrode members may not provide any signal to the outer members 26b having at least one circuit 26e. Each circuit can include at least one conductor 31. Such electrode members 26c may not be used for recording and/or transmitting any data to a measurement device 7. Such electrode members 26c may not be selected for use automatically due to their non-signal providing positioning. The selection of the electrode members 26c that contact the patient's scalp can occur automatically as data is only collected and provided by these electrode members 26c.

In some embodiments, some electrode members 26c at each hub 25 may contact the patient's scalp and conduct sensed data concerning the patient's response to the evoke event induced via the shock to the outer member 26b of the hub 25. The outer member 26b may have a selection circuit that only transmits the electrode member 26c that provides the strongest signal or may only transmit electrode member 26c data from a pre-selected number of the electrode members 26c that have a signal strength over a pre-selected threshold for transmission to the measurement device 7 for selecting which electrode members 26c of the electrode array to utilize for measuring patient body data concerning the evoke event, or "shock". Such a selection can also occur when the electrode member 26c is used for passively monitoring electrical activity of a patient's brain for EEG.

In yet other embodiments, the electrode members 26c at each hub 25 that contact a patient's scalp and collect data concerning patient electrical brain activity and subsequently transmit data to the outer member 26b can have that data transmitted to the measurement device 7 via a transmission circuit of the outer member 26b. The measurement device 7 can receive all this data and utilize all that data or only a pre-selected set of this data for comparing data from left-side electrode hubs 25 to the data received from the right-side electrode hubs 25. All received data may be utilized or only data from each electrode member 26c that meets a pre-selected set of criteria may be used. This criteria can include signal strength for a corresponding pair of electrode members 26c of a corresponding pair of electrode hubs 25 being at or exceeding a particular threshold. The criteria can also include, or instead include, some other information (e.g. a detected impedance match between corresponding pairs, etc.). In yet other embodiments, electrode member pairs can be selected such that individual electrode members 26c of a hub can be matched with a specific electrode member 26c of a corresponding hub 25 at a mirror image location on the patient's head so that the electrode member pairs can be matched.

In some embodiments, the electrode members to be selected can be the electrode members 26c that have a signal strength that has a difference that is less than 10% of the average, or mean, signal strength for the electrode members of a hub or that is less than a 20% difference from the mean signal strength. Such selection can be used in embodiments that utilized impedance matching for the selection criteria for the electrode members 26c, for example.

The selection and grouping of corresponding electrode hubs 25 and/or electrode members 26c need not be limited to particular pairs. For example, multiple electrode members 26c from multiple different hubs 25 can be grouped together so that there is not just a pair of corresponding electrode members 26c that are selected or defined as corresponding with each other. For instance, corresponding electrode members 26c for each hub 25 can be selected to that particular electrode members 26c of multiple different hubs are selected to being within a corresponding set of electrode members 26c. For example, the left ear hub, front left hub, and rear left hub can each have an electrode member 26c (e.g. their electrode member having the strongest signal) within a first group of corresponding left side electrode members and the right ear hub, front right hub, and rear front hub can each have an electrode member in a second group of corresponding right side electrode members (e.g. each hub's electrode member having the strongest signal). The first and second groups of electrode members 26c can define a first set of corresponding right side and left side electrode members. Each such set can also be defined to further specify specific corresponding pairs within the first set (e.g. left and right ear hub electrode members can be a particular pair within the first set, etc.). There can be multiple such groupings for defining different sets of different electrode members for the left and right side hubs (e.g. a first set can have a grouping of the electrode members with the strongest signals, the second set can have a grouping of the electrode members with the second strongest signals, etc.). As discussed herein, identification information included in the electrode member data transmitted to the measurement device 7 can identify the location of each electrode member 26c or hub 25 for use in forming the different electrode member groupings and identification and selection of various pairs and/or sets of electrode members 26c.

In yet other embodiments, the measurement device 7 can be configured to select which left and right side electrode pairs or electrode member 26c pairs within different electrode hubs 25 on the patient's head to be used based on impedance matching to select the best sets of pairs. The "best" pairs that match impedance values from a pre-selection routine run via the measurement device before an evoke event is triggered in the patient can occur so that the pairs that have the best impedance match are used for collecting the patient data and transmitting that data to the measurement device 7. The criteria for selecting the best pairs can include selection of only a single best pair, the top two best pairs, the top three best pairs, or some other pre-selected number of "best" pairs that have the closest impedance matches. After the best pairs are selected, the patient may be "shocked" via passing a current or voltage through the patient and the electrode pairs that were selected can be used to record data relating to the patient's response to the "shock" event for transmission to the measurement device 7 so that a comparison of the responses the left and right sides of the patient's head had to the event can be made to determine whether the patient has undergone a stroke or seizure. Additionally (or as an alternative), the best pairs that are selected may be utilized to collect data for use in EEG prior to, after, and/or without involvement of any evoked potential being passed through the patient's body. When the patient is detected as having experienced a condition (e.g. a stroke), the patient can be routed by emergency care personnel or other health care personnel to the appropriate location within a care facility or to an appropriate care facility for treatment.

In some embodiments, the pairs of electrode members 26c or pairs of hubs 25 can be utilized to select a reference electrode hub (or reference electrode member 26c) and ground electrode hub 25 (or ground electrode member 26c) as well. Selecting which pair of electrode hubs 25 or electrode members 26c for use as ground and reference electrodes can decrease the likelihood of a bad test that could result from poorly placed reference electrode. The selection criteria made to select the reference and ground electrode hubs 25 of electrode members 26c of hubs 25 can be utilized prior to any testing or data recording being performed. The measurement device 7 can be configured to make such a selection based on at least one of the following selection criteria: electrode member pair or electrode hub pair having the closest impedance match between electrodes, electrode member pair or electrode hub pair having the strongest signals, and/or other criteria.

In some embodiments, each electrode hub 25 of the headgear 3 can have at least one LED indicator 261 that is configured to illuminate light in a particular color (e.g. green) when there is a good electrical connection between the patient's head and at least one electrode member 26c of the hub 25. If the electrical connection is below a first pre-selected threshold that may define a good connection, the LED indicator 261 may turn a second color (e.g. yellow) and if the electrical connection is below a second pre-selected threshold that is below the first threshold and may define a non-connection or an unsuitable connection, the LED indicator 261 may turn a third color (e.g. red).

In some embodiments, the first pre-selected threshold can be an electrical conductivity resistance threshold that is 5,000 ohms or a value in the range of 2,500 ohms to 10,000 ohms and the second pre-selected threshold can be an electrical conductivity resistance threshold of 30,000 ohms or a value in the range of 15,000 ohms to 40,000 ohms. Other values could alternatively be selected for the first and second pre-selected thresholds to account for a particular type of electrode configuration or to meet a particular set of design criteria. In yet other embodiments, the threshold may be a value that is in another unit of measure (e.g. volts or amps). The unit of measure that is utilized for the threshold detection values can be based on the type of sensor or detection methodology utilized for assessing the electrically conductive connection between an electrode member 26c and the patient's scalp 30.

For embodiments that may select electrode hubs or electrode members 26c for use in a test of a neurological condition based on impedance matching, the color indication thresholds can be based on an evaluation of how electrode members deviate from an average value instead of using an absolute value threshold value. Such thresholds can be utilized for LED indicator 261 illumination and/or for illumination of electrode indicia 9c or other indicia that may be displayed to a user for helping the user assess the acceptability of the position of headgear 3 or connection quality of electrode members 26c as discussed herein. For instance, if the electrode members of a particular hub include electrode members that are within 10% of a mean value for the entire array of electrodes, the indicator for a particular hub may be illuminated in a first color (e.g. green). If the electrode members of a particular hub include electrode members that are within 20% of a mean value for the entire array of electrodes and also have a difference that is greater than 10%, the indicator for a particular hub may be illuminated in a second color (e.g. yellow). If the electrode members of a particular hub include electrode members that all have a difference that is greater than 20% from the mean value for the entire array of electrodes, the indicator for that electrode hub may be illuminated in a third color (e.g. red). Such thresholds can be used for illumination of LED indicators 261 and/or electrode indicia 9c, for example.

It should be appreciated that in some embodiments there may be a single LED indicator 261 for each electrode hub 25 and in other embodiments there may be more than one such indicator for a hub 25 (e.g. there may be an indicator for each electrode member 26c of a hub that is connected to outer member 26b of the hub to be visible when the patient wears headgear 3 to provide a visual indication of which electrode hubs 25 or electrode members 26c are in a desired position and/or have a suitable connection for use in an evaluation. The electrode indicia 9c utilized in different displays can also be provided so that there is a single indicator for each hub 25 or so that there is a single indicator for each electrode member 26c.

The use of electrode hubs having multiple electrode members (which may all be independently moveable for contacting a patient scalp) can be a useful approach for using the law of big numbers to try and obtain a sufficiently good (or acceptable) connection at a pre-selected set of corresponding left and right side locations on patient for performing a neurological condition detection test utilizing an evoke potential event (e.g. a "shock"). by use of a large number of electrode members via the hubs, the law of big numbers and randomness can be leveraged to allow for high likelihood that headgear 3 positioning will result in providing a sufficient electrical conductivity connection between the neurological testing apparatus (e.g. measurement device 7) and the electrode sensors of the apparatus (e.g. hubs 25 and/or electrode members 26c) used to evaluate a patient's response for assessing the patient's condition. This can allow for a more reliable use of the apparatus and avoid the need for running multiple tests on a patient to assess the patient's condition, which can be of particular importance in emergency situations in which delays in a patient receiving care at an appropriate care facility can have dire health consequences.

It should be appreciated that different embodiments of an electrode array, electrode headgear, neurological condition detection device can utilize different arrangements to meet a particular set of design criteria. For instance, it should be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement. Therefore, while certain exemplary embodiments of headgear, electrodes, electrode arrays, neurological condition detection mechanisms, and methods of making and using the same have been shown and described above, it is to be distinctly understood that the invention is not limited thereto but may be otherwise variously embodied and practiced within the scope of the following claims.

What is claimed is:

1. An electronic device comprising:
   a processor connected to non-transitory memory;
   a housing, the processor and the memory within the housing:
   a representation of a patient head defined on the housing with a centerline extending from a first side of the representation of the patient head to a second side of the representation of the patient head, the representation of the patient head also having a third side between the first side and the second side and a fourth side between the first side and the second side, the fourth side being opposite the third side;
   a plurality of first light emitting devices (LEDs) positioned on the housing inside the representation of the patient head, the first LEDs between the third side of the representation and the centerline;
   a plurality of second LEDs positioned on the housing inside the representation of the patient head, the second LEDs between the fourth side of the representation and the centerline;
   wherein each of the first LEDs is associated with a respective electrode of a first set of electrodes that are connectable to the electronic device and each of the second LEDs is associated with a respective electrode of a second set of electrodes connectable to the electronic device, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient;
   the processor configured to:

illuminate each of the first LEDs in a first color when a first signal generated based on the first biosignals associated with that first LED is at a first pre-selected threshold, in a second color when the first biosignal is below the first pre-selected threshold and above a second pre-selected threshold, and in a third color when the first signal is below the second pre-selected threshold indicating adjustment of the position of the corresponding first electrode is needed; and illuminate each of the second LEDs in the first color when a second signal generated based on the second biosignals associated with that second LED is at the first, pre-selected threshold, in the second color when the second signal is below the first pre-selected threshold and above the second pre-selected threshold, and in the third color when the second signal is below the second pre-selected threshold indicating adjustment of the position of the corresponding second electrode is needed;

wherein:

the first pre-selected threshold is defined to indicate an electrical conductivity connection acceptable for measuring the first biosignals of the patient;

the second pre-selected threshold is defined to indicate the electrical conductivity connection that is unacceptable for measuring the second biosignals of the patient; and wherein the first color differs from the second color and the first color differs from the third color and the second color differs from the third color.

2. The electronic device of claim 1, wherein: each of the first LEDs and each of the second LEDs being illuminatable in the first color, the second color, and the third color prior to the patient receiving an induced voltage via the electronic device for measuring a response the patient has to the induced voltage.

3. The device of claim 1, comprising:

an electrode positioning indication map positioned on the housing that includes a first line intersected by a second line positioned on the housing to define a plurality of quadrants between the first line and the second line, a plurality of third LEDs positioned on the housing on and along the first line; a plurality of fourth LEDs position on the housing on and along the second line.

4. The device of claim 3, comprising:

a central fifth LED positioned on the housing at a central section at which the first line intersects the second line.

5. The device of claim 4, comprising:

a plurality of quadrant LEDs positioned on the housing in the quadrants.

6. The electronic device of claim 1, comprising:

a display connected to the housing, the display configured to illustrate an electrode positioning indication map that includes a first line intersected by a second line positioned on the housing to define a plurality of quadrants between the first line and the second line.

7. An electronic device comprising:

a processor connected to non-transitory memory;

a housing, the processor and the memory within the housing;

a representation of a patient head defined on the housing with a centerline extending from a first side of the representation of the patient head to a second side of the representation of the patient head, the representation of the patient head also having a third side between the first side and the second side and a fourth side between the first side and the second side, the fourth side being opposite the third side;

a plurality of first light emitting devices (LEDs) positioned on the housing inside the representation of the patient head, the first LEDs between the third side of the representation and the centerline;

a plurality of second LEDs positioned on the housing inside the representation of the patient head, the second LEDs between the fourth side of the representation and the centerline;

wherein each of the first LEDs is associated with a respective electrode of a first set of electrodes that are connectable to the electronic device and each of the second LEDs is associated with a respective electrode of a second set of electrodes connectable to the electronic device, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient; and an electrode positioning indication map positioned on the housing that includes a first line intersected by a second line positioned on the housing to define a plurality of quadrants between the first line and the second line;

a plurality of third LEDs and a plurality of fourth LEDs are positioned on the housing on and along the first line and the second line, respectively, wherein the third LEDs and fourth LEDs are associated with the first electrodes and the second electrodes that are communicatively connectable to the electronic device; and the processor configured to:

illuminate each of the first LEDs in a first color when a first signal generated based on the first biosignals of the respective first LED is at a first pre-selected threshold; and illuminate each of the second LEDs in the first color when a second signal generated based on the second biosignals of the respective second LED is at the first pre-selected threshold;

illuminate at least one of the third and at least one of the fourth LEDs to indicate direction of positional adjustment of the first and second electrodes based upon data generated from the first signals and/or the second signals.

8. The device of claim 7, wherein the first electrodes and the second electrodes are attached to a headgear and the direction of positional adjustment indicated by illumination of the at least one of the third LEDs and the at least one of the fourth LEDs indicates a direction at which the headgear is to be adjusted to position the first electrodes and the second electrodes for measuring the first and second biosignals from a head of the patient.

9. An electronic device comprising:

a processor connected to non-transitory memory;

a housing, the processor and the memory within the housing;

a representation of a patient head defined on the housing with a centerline extending from a first side of the representation of the patient head to a second side of the representation of the patient head, the representation of the patient head also having a third side between the first side and the second side and a fourth side between the first side and the second side, the fourth side being opposite the third side;

a plurality of first light emitting devices (LEDs) positioned on the housing inside the representation of the patient head, the first LEDs between the third side of the representation and the centerline;

a plurality of second LEDs positioned on the housing inside the representation of the patient head, the second LEDs between the fourth side of the representation and the centerline;

wherein each of the first LEDs is associated with a respective electrode of a first set of electrodes that are connectable to the electronic device and each of the second LEDs is associated with a respective electrode of a second set of electrodes connectable to the electronic device, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient;

the processor configured to:

illuminate each of the first LEDs in a first color when a first signal generated based on the first biosignals associated with that first LED is at a first pre-selected threshold, in a second color when the first biosignal is below the first pre-selected threshold and above a second pre-selected threshold, and in a third color when the first signal is below the second pre-selected threshold indicating adjustment of the position of the corresponding first electrode is needed; and illuminate each of the second LEDs in the first color when a second signal generated based on the second biosignals associated with that second LED is at the first, pre-selected threshold, in the second color when the second signal is below the first pre-selected threshold and above the second pre-selected threshold, and in the third color when the second signal is below the second pre-selected threshold indicating adjustment of the position of the corresponding second electrode is needed;

wherein:

the first pre-selected threshold is defined to indicate an electrical conductivity connection acceptable for measuring the first biosignals of the patient;

the second pre-selected threshold is defined to indicate the electrical conductivity connection that is unacceptable for measuring the second biosignals of the patient; and wherein the first color differs from the second color and the first color differs from the third color and the second color differs from the third color;

wherein the display is configured to illuminate at least one indicia on and along the first line of the electrode positioning map and at least one indicia on and along the second line of the electrode positioning map to indicate a direction of positional adjustment of the first electrodes and the second electrodes based on data that is generated based on the first biosignals and the second biosignals that the device receives from the first and second electrodes, the first and second electrodes being communicatively connectable to the device.

10. The device of claim 9, comprising:

a headgear having an array of electrodes communicatively connectable to the processor, the array of electrodes including the first electrodes and the second electrodes; and wherein the display is configured to illuminate at least, one indicia on and along the first line of the electrode positioning map and at least one indicia on and along the second line of the electrode positioning map to indicate a direction of positional adjustment for the first and second electrodes that are communicatively connectable to the electronic device based on data that is generated based on the first biosignals and the second biosignals that is received from the first and second electrodes.

11. An electronic device comprising:

a processor connected to non-transitory memory;

a housing, the processor and the memory within the housing;

a display connected to the housing the display configured to illustrate a visible representation of a patient head with a centerline extending from a first side of the representation of the patient head to a second side of the representation of the patient head, the representation of the patient head also having a third side between the first side and the second side and a fourth side between the first side and the second side, the fourth side being opposite the third side;

the display configured to illustrate visible first indicia inside the representation of the patient head between the third side of the representation and the centerline;

the display configured to illustrate visible second indicia inside the representation of the patient head the second visible indicia between the fourth side of the representation and the centerline;

the display configured such that each of the visible first indicia is associated with a respective electrode of a first set of electrodes that are connectable to the electronic device and each of the visible second indicia is associated with a respective electrode of a second set of electrodes connectable to the electronic device, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient;

wherein the processor is configured such that the display is configured to:

illuminate each of the visible first indicia in a first color when a first signal generated based on the first biosignals associated with that first indicia is at a first pre-selected threshold;

illuminate each of the visible second indicia in the first color when a second signal generated based on the second biosignals associated with that second indicia is at the first pre-selected threshold;

illuminate each of the visible first indicia in a second color when the first signal is below the first pre-selected threshold and above a second pre-selected threshold; and illuminate each of the visible second indicia in the second color when the second signal is below the first pre-selected threshold and above the second pre-selected threshold;

illuminate each of the visible first indicia in a third color when the first signal is below the second pre-selected threshold indicating adjustment of the position of the corresponding first electrode is needed;

illuminate each of the visible second indicia in the third color when the second signal is below the second pre-selected threshold indicating adjustment of the position of the corresponding second electrode is needed;

wherein the first color differs from the second color and the first color differs from the third color and the second color differs from the third color; and the first pre-selected threshold is defined to indicate an electrical conductivity connection acceptable for measuring the first biosignals of the patient; the second pre-selected threshold is defined to indicate the electrical conductivity connection that is unacceptable for measuring the second biosignals of the patient.

12. The electronic device of claim 11, wherein:

the first pre-selected threshold defined to indicate an electrical conductivity connection is acceptable for measuring biosignals of a patient, the second pre-selected threshold defined to indicate that the electrical conductivity connection is unacceptable for measuring biosignals of the patient.

13. A method of indicating positional adjustment for headgear attached to an array of electrodes, the method comprising:

communicatively connecting an electronic device to an array of electrodes attached to headgear, the array of electrodes comprising a set of first electrodes and a set of second electrodes, visible first indicia associated with a respective electrode of the set of first electrodes and visible second indicia associated with a respective electrode of the set of second electrodes, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient;

displaying a visible representation of a patient head defined on the housing with a centerline extending from a first side of the representation of the patient head to a second side of the representation of the patient head, the representation of the patient head also having a third side between the first side and the second side and a fourth side between the first side and the second side, the fourth side being opposite the third side;

displaying an electrode positioning indication map positioned on a housing that includes a first line intersected by a second line positioned on the housing to define a plurality of quadrants between the first line and the second line, positional indicia along the first line of the electrode positioning map and positional indicia along the second line of the electrode positioning map associated with the first electrodes and the second electrodes that are communicatively connected to the electronic device;

illuminating each of the visible first indicia in a first color when a first signal generated based on the first biosignals associated with that first indicia is at a first pre-selected threshold;

illuminating each of the visible second indicia in the first color when a second signal generated based on the second biosignals associated with that second indicia is at the first pre-selected threshold; and illuminating at least one of the positional indicia along the first line of the electrode positioning map and at least one of positional indicia along the second line of the electrode positioning map to indicate direction of positional adjustment of the first and second electrodes based upon data generated from the first signals and/or the second signals.

14. A method of indicating positional adjustment for headgear attached to an array of electrodes, the method comprising:

communicatively connecting an electronic device to an array of electrodes attached to headgear, the array of electrodes comprising a set of first electrodes and a set of second electrodes, visible first indicia associated with a respective electrode of the set of first electrodes and visible second indicia associated with a respective electrode of the set of second electrodes, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient;

displaying a visible representation of a patient head defined on the housing with a centerline extending from a first side of the representation of the patient head to a second side of the representation of the patient head, the representation of the patient head also having a third side between the first side and the second side and a fourth side between the first side and the second side, the fourth side being opposite the third side;

displaying an electrode positioning indication map positioned on a housing that includes a first line intersected by a second line positioned on the housing to define a plurality of quadrants between the first line and the second line, positional indicia along the first line of the electrode positioning map and positional indicia along the second line of the electrode positioning map associated with the first electrodes and the second electrodes that are communicatively connected to the electronic device;

illuminating each of the visible first indicia in a first color when a first signal generated based on the first biosignals associated with that first indicia is at a first pre-selected threshold;

illuminating each of the visible second indicia in the first color when a second signal generated based on the second biosignals associated with that second indicia is at the first pre-selected threshold; and illuminating at least one of the positional indicia along the first line of the electrode positioning map and at least one of positional indicia along the second line of the electrode positioning map to indicate direction of positional adjustment of the first and second electrodes based upon data generated from the first signals and/or the second signals;

adjusting the headgear in the direction of positional adjustment indicated by the illumination of the at least one positional indicia along the first line of the electrode positioning map and the illumination of the at least one positional indicia along the second line of the electrode positioning map;

after the adjusting of the headgear, checking all visible first indicia, and checking all visible second indicia; the checking performed to confirm that all visible first indicia and all visible second indicia are illuminated in the first color after the adjusting of the headgear is performed.

15. A method of indicating positional adjustment for headgear attached to an array of electrodes, the method comprising:

communicatively connecting an electronic device to an array of electrodes attached to headgear, the array of electrodes comprising a set of first electrodes and a set of second electrodes, visible first indicia associated with a respective electrode of the set of first electrodes and visible second indicia associated with a respective electrode of the set of second electrodes, each of the first electrodes configured to measure first biosignals of a patient's response to induced voltage to be transmitted to the patient, the first biosignals being detectable by the first electrodes via an electrically conductive connection between the first electrodes and a body of the patient, each of the second electrodes configured to measure second biosignals of the patient's response to the induced voltage to be transmitted to the patient, the second biosignals being detectable by the second electrodes via an electrically conductive connection between the second electrodes and the body of the patient;

displaying a visible representation of a patient head defined on the housing with a centerline extending from a first side of the representation of the patient head to a second side of the representation of the patient head, the representation of the patient head also having a third side between the first side and the second side and a fourth side between the first side and the second side, the fourth side being opposite the third side;

displaying an electrode positioning indication map positioned on a housing that includes a first line intersected by a second line positioned on the housing to define a plurality of quadrants between the first line and the second line, positional indicia along the first line of the electrode positioning map and positional indicia along the second line of the electrode positioning map associated with the first electrodes and the second electrodes that are communicatively connected to the electronic device;

illuminating each of the visible first indicia in a first color when a first signal generated based on the first biosignals associated with that first indicia is at a first pre-selected threshold;

illuminating each of the visible second indicia in the first color when a second signal generated based on the second biosignals associated with that second indicia is at the first pre-selected threshold; and illuminating at least one of the positional indicia along the first line of the electrode positioning map and at least one of positional indicia along the second line of the electrode positioning map to indicate direction of positional adjustment of the first and second electrodes based upon data generated from the first signals and/or the second signals;

wherein the first pre-selected threshold indicates sufficient connection to the head of the patient to facilitate testing of the patient via use of the headgear for collection of the first and second biosignals from the head of the patient.

* * * * *